United States Patent [19]
Yasui et al.

[11] Patent Number: 5,746,695
[45] Date of Patent: May 5, 1998

[54] FRONT END STRUCTURE OF ENDOSCOPE

[75] Inventors: Naoki Yasui; Hiroshi Iwata; Hiroyuki Katsurada; Keiji Ito; Takayuki Ogino, all of Tokyo, Japan

[73] Assignee: Asahi Kogaku Kogyo Kabushiki Kaisha, Tokyo, Japan

[21] Appl. No.: 711,875

[22] Filed: Sep. 12, 1996

Related U.S. Application Data

[62] Division of Ser. No. 342,250, Nov. 18, 1994, abandoned.

[30] Foreign Application Priority Data

| Nov. 18, 1993 | [JP] | Japan | 5-288567 |
| Nov. 26, 1993 | [JP] | Japan | 5-296530 |
| Dec. 1, 1993 | [JP] | Japan | 5-301426 |
| Jan. 24, 1994 | [JP] | Japan | 6-5491 |
| Mar. 15, 1994 | [JP] | Japan | 6-42987 |
| Mar. 15, 1994 | [JP] | Japan | 6-42988 |

[51] Int. Cl.$^6$ .................................. A61B 1/04
[52] U.S. Cl. .................. 600/127; 600/121; 600/125; 600/129
[58] Field of Search .................. 600/121, 123, 600/125, 127, 129, 153, 156, 157, 158, 203, 187, 205, 188

[56] References Cited

U.S. PATENT DOCUMENTS

| 4,881,810 | 11/1989 | Hasegawa | 600/127 |
| 5,193,525 | 3/1993 | Silverstein et al. | 128/4 |
| 5,257,617 | 11/1993 | Takahashi | 128/4 |
| 5,536,236 | 7/1996 | Yabe et al. | 600/129 X |

FOREIGN PATENT DOCUMENTS

| 64-6804 | 2/1989 | Japan | 600/127 |
| 4-14617 | 5/1992 | Japan | 600/127 |
| 6-14865 | 1/1994 | Japan | 600/127 |

*Primary Examiner*—Beverly M. Flanagan
*Attorney, Agent, or Firm*—Kane, Dalsimer, Sullivan, Kurucz, Levy, Eisele and Richard, LLP

[57] ABSTRACT

A cap assembly of a front end of an inserting portion of an endoscope and a cap to be attached to the front end of the endoscope, comprising; a first engaging portion provided on the front end of the inserting portion of the endoscope; and, a second engaging portion provided on the cap being disengageably engaged with the first engaging portion of the endoscope. The front end of the inserting portion of the endoscope is provided with a projection whose diameter being smaller than a diameter of the front end, the projection being connected to the front end through a stepped portion.

3 Claims, 28 Drawing Sheets

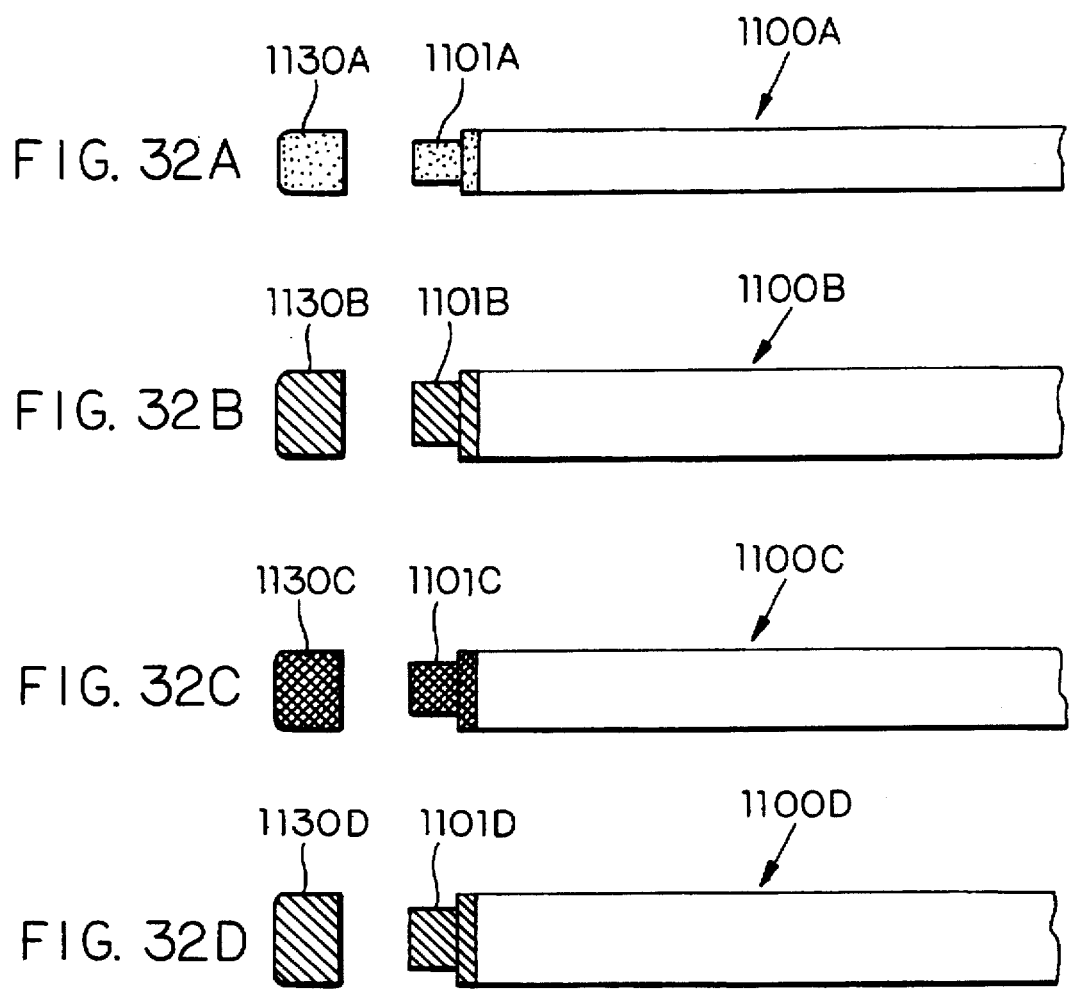

5,746,695

FRONT END STRUCTURE OF ENDOSCOPE

This is a division of application Ser. No. 08/342,250, filed Nov. 18, 1994, abandoned.

BACKGROUND OF THE INVENTION

1. Field of the Invention

The present invention relates to a front end structure of an endoscope having a nozzle from which fluid such as air or water can be injected toward an outer surface of a viewing window of the endoscope.

2. Description of Related Art

A nozzle provided at the front end of an endoscope is preferably detachable, so that the nozzle can be detached from the endoscope to allow cleaning of an air supply tube or water supply tube, etc., using a brush to remove foreign matter from the air supply tube or water supply tube after the endoscope has been used. To this end, in a conventional endoscope, the base portion of the nozzle is detachably fitted or inserted into the open end of the air or water supply tube at the front end of the endoscope and secured therein by a screw or the like.

However, it is necessary to deeply recess the front end of the endoscope to fit or insert the nozzle into the open end of the air or supply tube. Consequently, it is difficult to clean the deep recess after the nozzle is detached, so that filth or foreign matter tends to remain in the recess. The residual foreign matter is insanitary to a patient or causes a patient to be infected therewith.

To prevent this, it has been proposed, for example in Japanese Examined Utility Model Publication No. 4-804 to provide an air or water supply port at the front end of the endoscope to be in parallel with the viewing window, wherein an end cap of an elastic material such as rubber, which can be detachably attached to the outer peripheral surface of the front end of the endoscope is integrally provided with an inwardly projecting nozzle in the form of eaves to face the air or water supply port.

Namely, the nozzle is integrally formed with the elastic end cap and can be easily attached to or detached from the front end of the endoscope. Moreover, the opening of the air or water supply port formed at the front end of the endoscope can be easily cleaned after the endoscope is used.

Nevertheless, in the proposal, since the end cap which is made of an elastic material is attached at the outer peripheral surface thereof to the front end of the endoscope, and the nozzle piece integral with the end cap projects inwardly therefrom, the nozzle piece can be elastically deformed (twisted) to some extent.

Consequently, the nozzle is elastically bent upward when a pneumatic or hydraulic pressure by the air or water injected from the air or water supply port is exerted on the nozzle, thus resulting in a failure to inject the air or water onto the surface of the viewing window. Thus, any foreign matter on the surface of the viewing window cannot be removed during the operation of the endoscope, which results in a deterioration of the image produced by the endoscope.

An end cap can be made from a resilient material and detachably attached to the outer peripheral surface of the front end body of the endoscope.

In such a front end structure of an endoscope, the end cap must be attached to the front end body at a correct relative angular position in a rotational direction without allowing it to be accidentally detached from the front end body.

To this end, there is provided a positioning means which is comprised of, for example a matching engageable projection and recess between the end cap and the front end body to determine a relative angular position therebetween in the rotational direction and a detachment preventing engaging means which is comprised of, for example a matching engageable projection and recess between the end cap and the front end body to prevent the end cap from being accidentally detached from the front end body.

When the end cap is attached to the front end body, an elastic and outward deformation of the end cap takes place before the projection of the detachment preventing engaging means is inserted in the recess thereof to thereby complete the engagement of the projection in the recess.

In this state, the front end body is fastened by the end cap owing to the elastic force caused by the elastic deformation of the end cap. Consequently, there is a large frictional resistance in the fastened portion, so that a strong force is necessary to rotate the end cap relative to the front end body against the frictional resistance.

However, in a conventional front end structure of an endoscope, when the end cap is fitted on the front end body of the endoscope, the end cap is elastically expanded before the relative angular position between the end cap and the front end body is determined by the positioning means.

Consequently, when the relative angular position is determined by the positioning means, it is necessary to exert a large torsional force on the end cap or the front end body in the rotational direction, and hence there is a possibility that the front end of the inserting portion of the endoscope is broken.

The projection and recess for preventing the end cap from being detached from the front end body are formed on the outer peripheral surface of the substantially cylindrical front end body of the endoscope and on the inner peripheral surface of the end cap which is, for example, rubber-molded, respectively, so that they can be easily manufactured.

There are different kinds of endoscopes having front end bodies to which end caps are detachably attached, depending on the intended purpose. In conventional endoscopes, the outer surface of the front end body and the outer surface of the end cap have the same color, such as black or blackish color.

For instance, in a hospital, different kinds of endoscopes are sometimes prepared and used on the same day for different patients.

Therefore, there is a possibility that an end cap which has been detached from an associated endoscope to wash, clean and disinfect the latter and the end cap after the endoscope has been used is attached to the wrong endoscope.

If an end cap is compatible to different kinds of endoscopes, each having an identical front end body, there is no problem, since the end cap can be equally attached to the front end body. However, in the case of an incompatible end cap, if the end cap is attached to a front end body of a wrong endoscope, an excessive external force may be applied to the front end body, thus resulting in a breakage thereof.

Further more, if the end cap and the front end body have the same color, it is hard to see the boundary portion between the end cap and the exposed surface of the front end body.

SUMMARY OF THE INVENTION

The primary object of the present invention is to provide a front end structure of an endoscope having a resilient end cap which is integrally provided with a nozzle which can be detachably attached to a front end body of the endoscope, wherein no upward movement (swing) of the nozzle occurs during the injection of fluid, so that the fluid can be correctly injected onto the surface of the viewing window.

It is an object of the present invention to provide a front end structure of an endoscope in which it is not necessary to apply a large rotational force to mount the end cap to the front end body, thus resulting in no breakage of the front end of the endoscope.

A particular object of the present invention to provide a front end structure of an endoscope including a front end body which is provided on the outer peripheral surface thereof with a recess and an end cap which is provided on the inner peripheral surface thereof with a recess in which a projection can be fitted to prevent the end cap from being accidentally detached from the front end body, wherein it is not necessary to apply a strong rotational force to the end cap upon attachment of the latter to the front end body, thus resulting in no breakage of the front end body.

Another object of the present invention is to provide a front end structure of an endoscope, in which an end cap to be attached to a front end of an associated endoscope can be easily and visually identified, so that there is no deinger that the front end of the endoscope can be broken due to the attachment of the wrong end cap to the endoscope.

According to one aspect of the present invention there is provided a cap assembly for a front end of an inserting portion of an endoscope and a cap to be attached to the front end of the endoscope, comprising; a first engaging portion provided on the front end of the inserting portion of the endoscope; and, a second engaging portion provided on the cap being disengageably engaged with the first engaging portion of the endoscope.

In one embodiment, the front end of the inserting portion of the endoscope is provided with a projection whose diameter being smaller than the diameter of the front end fo the body. The projection being connected to the front end through a stepped portion.

Preferably, at least a part of an outer surface of the front end of the inserting portion is colored by a same color and/or pattern as at least a part of an outer surface of the end cap, and wherein there are different colors and/or pattrens for incompatible kinds of end caps.

According to another aspect of the invention, there is provided a front end structure of an endoscope comprising: a front end body which is provided on a front end surface thereof with a partial projection which being provided on a projecting end surface thereof with a viewing window and an illuminating window, the front end surface being provided with a plurality of fluid outlet ports opening therein, an end cap of a resilient material having a lower end surface which comes into close contact with the front end surface of the front end body and an upper end surface which is substantially flush with the projecting end surface of the projection, the end cap being detachably attached to the front end body to fasten the projection at the outer peripheral surface of the front end body; and, a nozzle passage which is provided in the end cap to be connected to the fluid outlet port of the front end body and opens into the viewing window of the projection when the end case being mounted to the front end body.

It accordance with the invention, a front end structure of an endoscope including a front end body which is provided at a front end of an insertion portion of an endoscope comprising: a substantially cylindrical end cap of a resilient material which is detachably attached to the outer peripheral surface of the front end body; a positioning portion which is adapted to determine a relative angular position between the end cap and the front end body in a rotational direction; and, a combination of engageable projections and recesses provided on the front end body and the end cap to prevent the front end body from accidentally coming out of the end cap; wherein when the end cap is attached to the front end body, a determination of a relative angular position between the front end body and the end cap is carried out by the positioning portion prior to an elastic deformation of the end cap which is caused to establish an engagement of the engageable projection with the recess.

It accordance with the invention, a front end structure of an endoscope including a front end body which is connected to a front end of an inserting portion of an endoscope comprising: an end cap of a resilient material which is detachably attached to the front end body; and, a fluid passage which extends in the front end body and the end cap to discharge fluid to the outside; wherein the fluid passage is provided, on the opening end thereof in the front end body, with a connecting pipe, and the fluid passage being provided, on the opening end thereof in the end cap, with a connecting hole in which the connecting pipe can be fitted when the end cap is attached to the front end body.

It accordance with the invention, a front end structure of an endoscope, including a front end body which has a circular cross section and which is provided at a front end of an inserting portion of an endoscope, and a substantially cylindrical end cap of a resilient material, which is detachably attached to the front end body, comprising: a partial projection which is provided on the front end of the front end body to project forward, peripheral grooves provided on the outer peripheral surface of the projection and the outer peripheral surface of front end body; an insertion hole formed in the end cap so that the projection is fitted in the insertion hole; a plurality of projections provided on the end cap to be fitted in the peripheral groove provided on the front end body; wherein when the end cap is attached to the front end body from the front end of the front end body, the projection of the front end body is fitted in the insertion hole of the end cap to determine a relative angular position therebetween in the rotational direction, and thereafter, the projections of the end cap are fitted simultaneously in the groove of the front end body.

According to another aspect of the invention, there is provided a front end structure of an endoscope, including a front end body provided on a front end of an inserting portion of an endoscope, and an end cap which is detachably attached to the front end body, wherein at least a part of an outer surface of the front end body is colored by a same color as at least a part of an outer surface of the end cap, and wherein there are different colors for incompatible kinds of end caps.

According to still another aspect of the invention, there is provided a front end structure of an endoscope including a front end body which being connected to a front end of an insertion portion of an endoscope, an end cap of a resilient material which being detachably attached to the front end body from the front end side thereof, wherein the outer peripheral surface portion of the front end body adjacent to the rear end of the end cap being exposed to the outside when the end cap being attached to the front end body, and wherein the exposed outer peripheral surface of the front end body and the outer peripheral surface of the end cap have different colors at least at a boundary portion there between.

The present disclosure relates to subject matter contained in Japanese patent application Nos. 05-288567 (filed on Nov. 18, 1993), 05-296530 (filed on Nov. 26, 1993), 05-301426 (filed on Dec. 1, 1993), 06-5491 (filed on Jan. 24, 1994), 06-42987 (filed on Mar. 15, 1994) and 06-42988 (filed on Mar. 15, 1994) which are expressly incorporated herein by reference in its entirety.

DESCRIPTION OF THE PREFERRED EMBODIMENTS

Embodiments of the present invention will be discussed below in detail.

Figure 1:
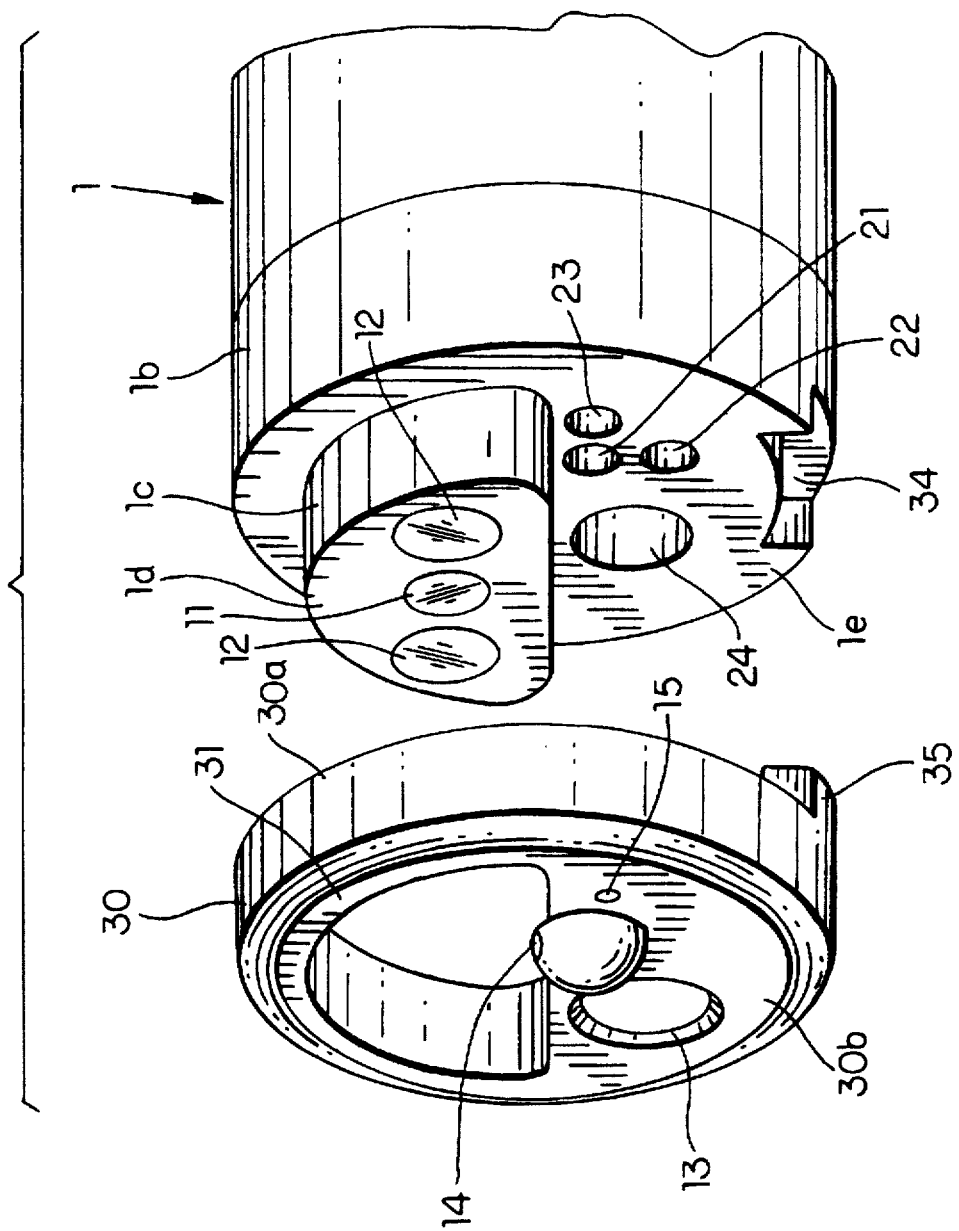
FIG. 1 is a perspective view of a front end structure of an endoscope according to a first embodiment of the present invention.
Figure 2:
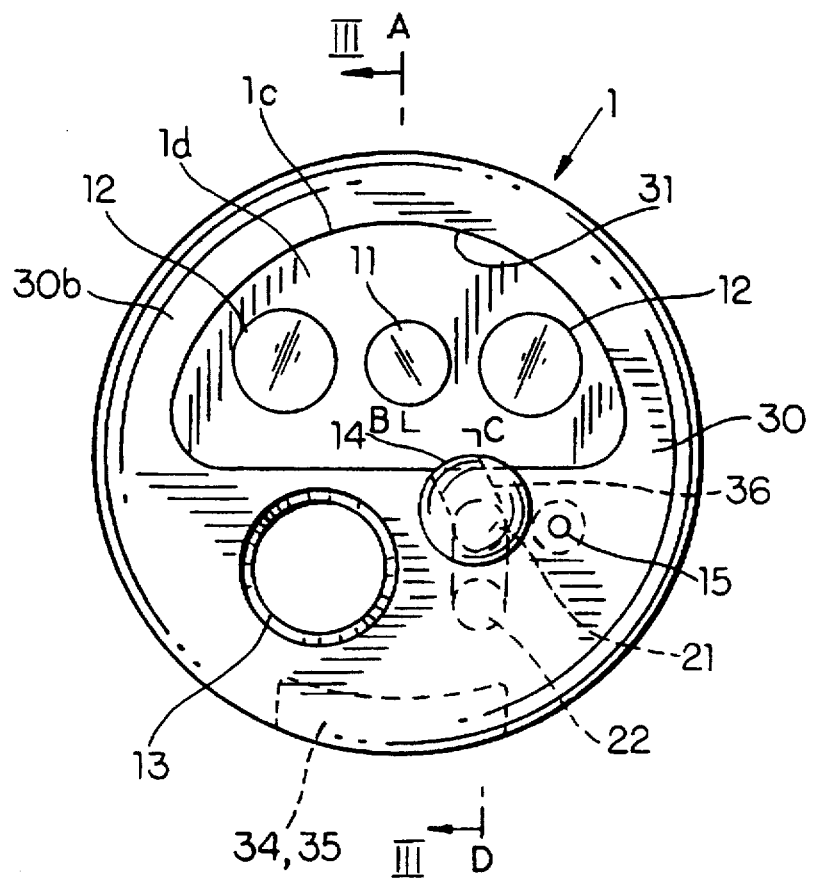
FIG. 2 is a front elevational view of FIG. 1.
Figure 3:
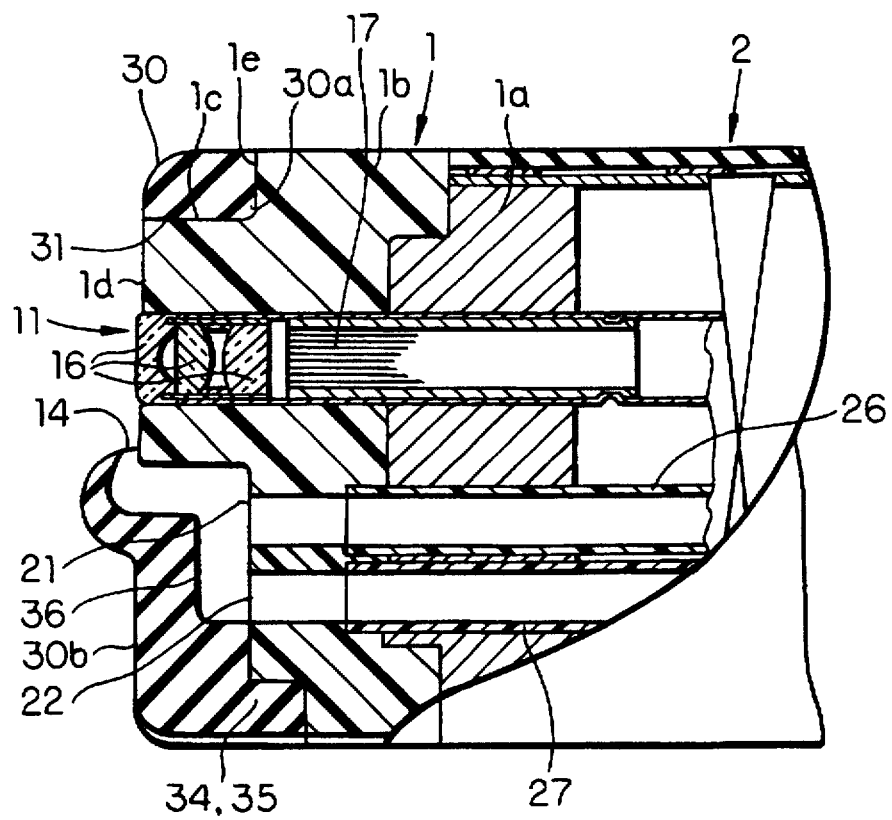
FIG. 3 is a sectional view taken along the line A-B-C-D in FIG. 2.
Figure 4:
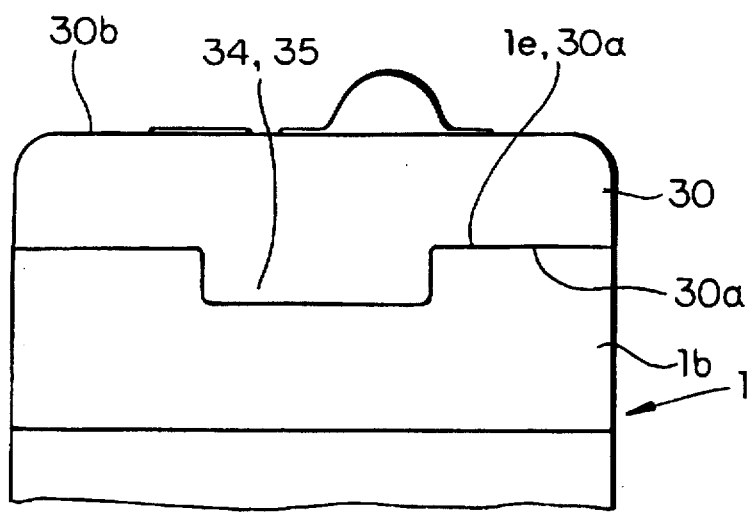
FIG. 4 is a bottom view of FIG. 1.

FIGS. 1 through 4 show a first embodiment of the present invention. FIG. 1 is a perspective view of a front end structure of an endoscope and an end cap detached from the front end of the endoscope; FIG. 2 is a front elevational view of a front end of an endoscope to which an end cap is attached; FIG. 3 is a sectional view taken along the line A-B-C-D in FIG. 2; and, FIG. 4 is a bottom view of FIG. 2.

As can be seen in FIG. 3, a front end body 1 is connected to a front end of a flexable portion 2 which is provided on the front end of an inserting portion. This inserting portion is in the form of an elongated flexible tube so as to bend in accordance with a remote control operation.

The front end body 1 is provided with a metal block portion 1a connected to the flexable portion 2, and an electrically insulating plastic portion 1b secured to the front end of the block portion 1a to cover the latter. An end cap 30 is attached to the front end body 1.

In the illustrated embodiment, the endoscope is a forward view type endoscope to view the forward direction of the longitudinal axis. The front end body 1 is provided on the front end surface thereof with a viewing window 11 and illuminating windows 12. The end cap 30 is provided with a forceps channel outlet hole 13, an air/water injection nozzle 14 which opens toward the viewing window 11 and which is formed by a hemispherical bulged body, and a jet flow injection nozzle 15 which opens in the viewing direction.

In a passage connected to the viewing window 11, there is an objective optical system 16 and an image receiving end of an image guiding fiber bundle 17, as shown in FIG. 3. There is an emitting end of a light guiding fiber bundle (not shown) in a passage connected to the illuminating windows 12. Note that the present invention can be applied to an electronic endoscope using a solid state image sensor which transmits an image represented by electric signals, or rigid endoscope, etc.

As can be seen, for example, in FIG. 1, the front end of the plastic portion 1b of the front end body 1 is provided on an end surface 1e thereof with a projection 1c which is formed by partially projecting the portion of the front end of the plastic portion 1b from the end surface 1e that includes the viewing window 11 and the illuminating windows 12. Namely, the viewing window 11 and the illuminating windows 12 are provided in the projection 1c. The projection 1c has a semicircular cross section.

The viewing window 11 and the illuminating windows 12 (the outer surfaces of the glass covers thereof) are flush with the outer end surface (projecting end surface) 1d of the projection 1c. The end surface 1e is provided with an air discharge port (air supply port) 21, a water discharge port (water supply port) 22, a jet flow injecting water supply port 23 and a forceps channel opening 24.

The air supply port 21 and the water supply port 22 are respectively connected to an air feed tube 26 and a water feed tube 27, inserted in and connected to the front end body 1 from the rearward direction, as may be seen in FIG. 3. Similarly, the jet flow injecting water supply port 23 and the forceps channel opening 24 are respectively connected to a jet flow injecting water feed tube (not shown) and a forceps channel (not shown).

The end cap 30 which is made of an elastic material, such as rubber and is detachably attached to the front end of the plastic portion 1b of the front end body 1.

The end cap 30 has an outer diameter identical to that of the front end body 1 and is shaped such that the annular end surface 30a thereof comes into close contact with the front end surface 1e of the front end body 1 and that the outer surface (front surface) of the end cap 30 is substantially flush with the projecting end surface 1d of the projection 1c, except for the hemispherical nozzle portion defining the nozzle 14.

The end cap 30 is provided with an insertion hole 31 whose shape corresponds to the projection 1c having a semicircular shape in cross section, so that when the end cap 30 is attached to the front end body 1, the projection 1c can be fitted in the insertion hole 31. The insertion hole 31 is slightly smaller than the cross sectional shape of the projection 1c.

Consequently, when the projection 1c is inserted in the insertion hole 31, the latter is elastically expanded, so that the projection 1c can be elastically pressed at the entire outer peripheral surface thereof due to the elastic force thus produced. In FIG. 1, the thickly hatched portions represent the surfaces of the insertion hole 31 and the projection 1c, on which the elastic fastening force acts.

With this arrangement, when the end cap 30 is positioned with respect to the front end body 1 and pressed against the same, the projection 1c is press-fitted in the insertion hole 31 to firmly connect the end cap 30 to the front end body 1. The firm connection is ensured by the elastic fastening force due to the press-fit of the projection 1c in the insertion hole 31, as may be seen in FIGS. 2 through 4.

Moreover, the front end body 1 and the end cap 30 are respectively provided on the peripheral edges thereof with a circumferential extending recess 34 and a corresponding projection 35 that can be engaged in the recess 34. The recess 34 and the projection 35 are visible from the outside. The visible recess 34 and projection 35 contribute to an easy positioning between the end cap 30 and the end body 1. When the end cap 30 is detached from the end body 1, the end cap 30 is moved forward (in left direction in FIG. 1) with a relatively strong force.

As shown in FIGS. 2 and 3, the end cap 30 is provided on the rear surface thereof with a nozzle passage 36 in the form of a recessed groove, which has a water and air tight connection to the air feed port 21 and the water feed port 22 when the end cap 30 is attached to the front end body 1.

The outlet end of the nozzle passage 36 defines the nozzle 14 which opens into the surface of the viewing window 11. The opening end of the nozzle 14 is located in the vicinity of the edge of the insertion hole 31, so that the opening end slightly extends into the insertion hole 31 as viewed from front (e.g., FIG. 2).

The end cap 30 is firmly connected to the front end body 1 owing to the elastic fastening force acting on the projection 1c from the inner wall of the insertion hole 31. Consequently, when air or water is injected from the nozzle 14, so that the nozzle 14 receives a reactionary force, the nozzle 14 can be immovably held in spite of the reactionary force. Namely, there is no displacement of the end cap 30 with respect to the end body 1.

Note that the jet flow injecting nozzle 15 and the forceps channel outlet opening 13 are formed in the end cap 30 to be in line with the jet flow water feed port 23 and the forceps channel port 24 of the end body 1 respectively.

Figure 5:
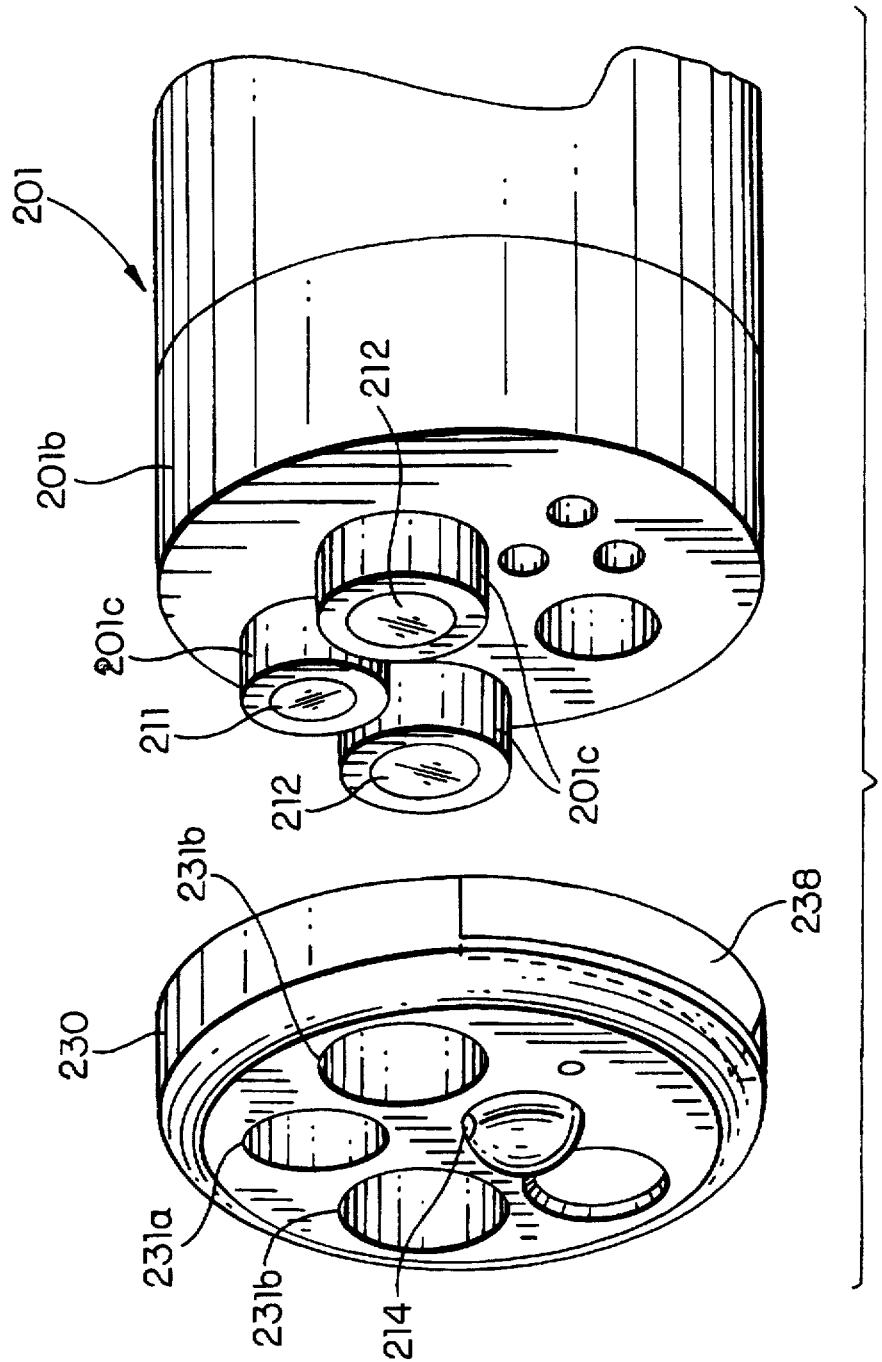
FIG. 5 is a perspective view similar to FIG. 1, according to a second embodiment of the present invention.
Figure 6:
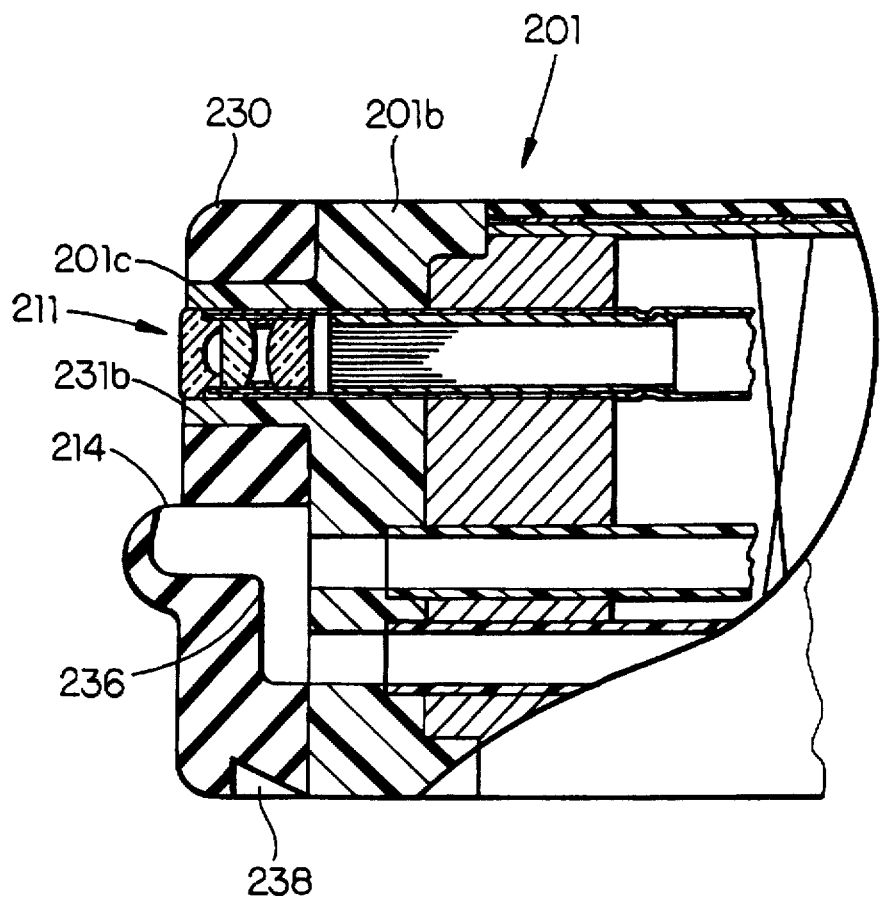
FIG. 6 is a side sectional view of a second embodiment shown in FIG. 5.

FIGS. 5 and 6 show a second embodiment of the present invention, in which a viewing window 211 and a illuminating windows 212 are respectively formed by independent cylindrical projections 201c. An end cap 230 is provided with three insertion holes 231a, 231b, 231c in which the corresponding projections 201c can be press-fitted. With this structure, the end cap 230 can be firmly connected to the end body 201. The three connections also ensure a certain positioning of the end cap 230 with respect to an end body 201.

In the second embodiment, a nozzle 214 is formed in a hemispherical bulged portion in the vicinity of two insertion holes 231b, 231b in which the projections 201c of the illuminating windows 212 are press-fitted and opens toward the viewing window 211.

The end cap 230 is provided on the peripheral edge portion thereof with a cut-away portion 238 which is visible from the outside, so that an operator can insert his or her finger in the cut-away portion 238 to detach the and cap 230 from the end body 201. Alternatively, it is possible to provide the cut-away portion 238 on the end body 201 in place of the end cap 230.

Figure 7:
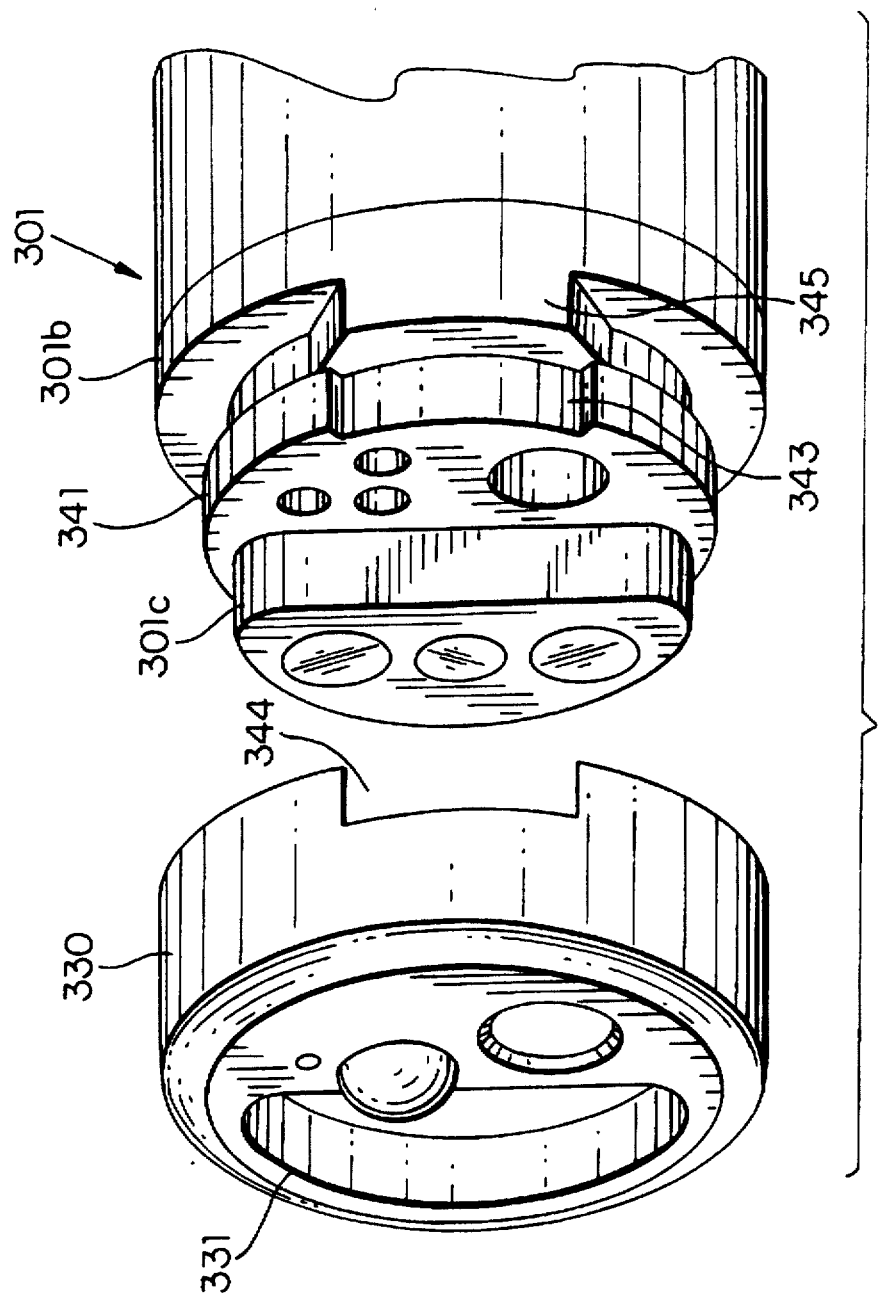
FIG. 7 is a perspective view similar to FIG. 1, according to a third embodiment of the present invention.
Figure 8:
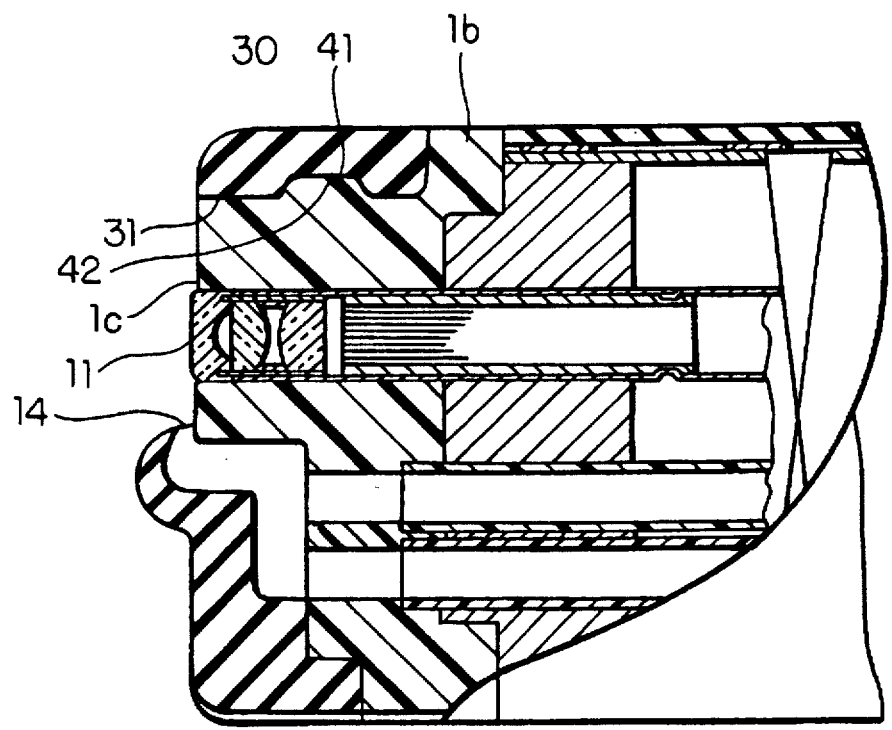
FIG. 8 is a side sectional view of a third embodiment shown in FIG. 7.

FIGS. 7 and 8 show a third embodiment of the present invention. In the third embodiment, a projection 301c of an end body 301 is press-fitted in a corresponding insertion hole 331 of an end cap 330, similar to the first embodiment. A plastic portion 301b is provided on the outer peripheral surface thereof with a projection 341 and the end cap 330 is provided on the inner peripheral surface thereof with a recess 342 in which the projection 341 can be fitted to prevent the end cap from being accidentally disengaged from the end body 301.

The projection 341 is provided with a cut-away portion 343.

The end cap 330 and the end body 301 are respectively provided with a visible recess 344 and a visible projection 345 which can be engaged in the recess 344, corresponding to the cut-away portion 343, so that the position of the cut-away portion 343 can be visually confirmed from the outside.

When an external force is exerted on the end cap 330 in the direction to move away from the end body 301 at the recess 344, the end cap can be more easily disengaged from the end body 301 than the remaining portion.

Figure 9:
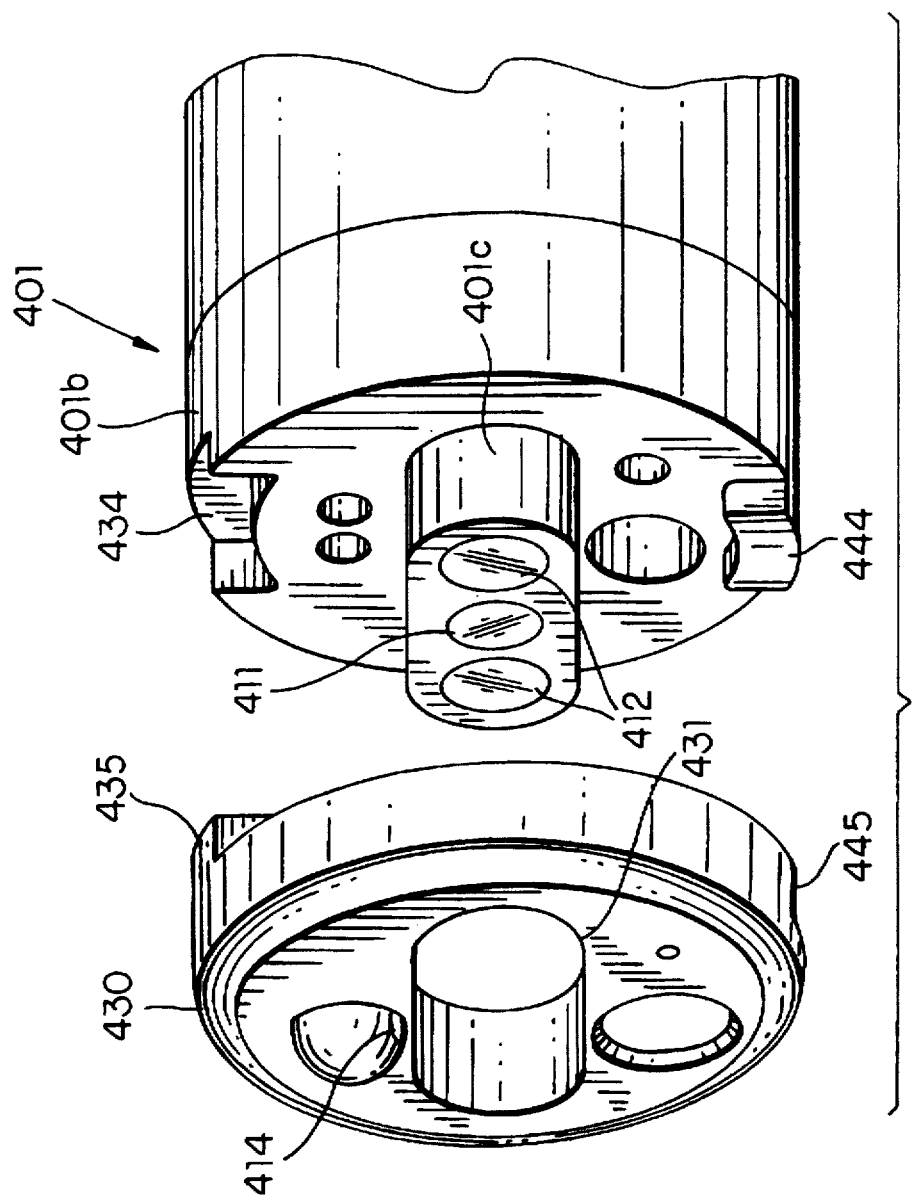
FIG. 9 is a perspective view similar to FIG. 1, according to a fourth embodiment of the present invention.

FIG. 9 shows a fourth embodiment of the present invention, in which a viewing window 411 and an illuminating windows 412 are aligned substantially along a diametral line of the circular windows 411 and 412 on an end surface of a projection 401c of a generally rectangular shape whose minor sides are rounded. The end cap 430 is provided with an elongated insertion hole 431 corresponding to a shape of the projection 401c.

The nozzle 414 is provided in the vicinity of the peripheral edge of the insertion hole 431 so as not to project from the peripheral edge of the insertion hole 431 into the insertion hole as viewed from front.

The visible recess 434 is provided on the end body 401 and the corresponding visible projection 435 which can be fitted in the recess 434 is provided on the end cap 430, respectively, similarly to the first embodiment. In addition, another recess 455 which is visible from the outside is provided on the end cap 430 and another projection 454 which is visible from the outside is provided on the front end body 401.

Consequently, upon mounting the end cap 430 to the end body 401, if the end cap 430 is attached to the end body 401 in a wrong direction by 180° (i.e., upside down), no engagement of the projections 435 and 454 in the corresponding recesses 434 and 455 can be established. Thus, only a correct positioning can be achieved.

As can be understood from the foregoing, according to the present invention, since the end cap can be firmly connected to the end body of the endoscope, and the fluid injecting nozzle is provided in the vicinity of the portion in which the firm connection is established between the end cap and the end body, no accidental movement of the nozzle occurs during the injection of the fluid from the nozzle. Hence, the fluid can be injected correctly onto the surface of the viewing window, so that any foreign matter applied to the surface of the viewing window can be removed by the injected fluid to obtain a clear image of an object to be viewed.

Moreover, the positioning means ensures that the end cap can be mounted to the end body of the endoscope at the correct position and direction.

Furthermore, if the specific portion at which the end cap can be removed from the end body of the endoscope when a small force is provided, the end cap can be easily detached from the end body of the endoscope without breaking the front end body.

Figure 10:
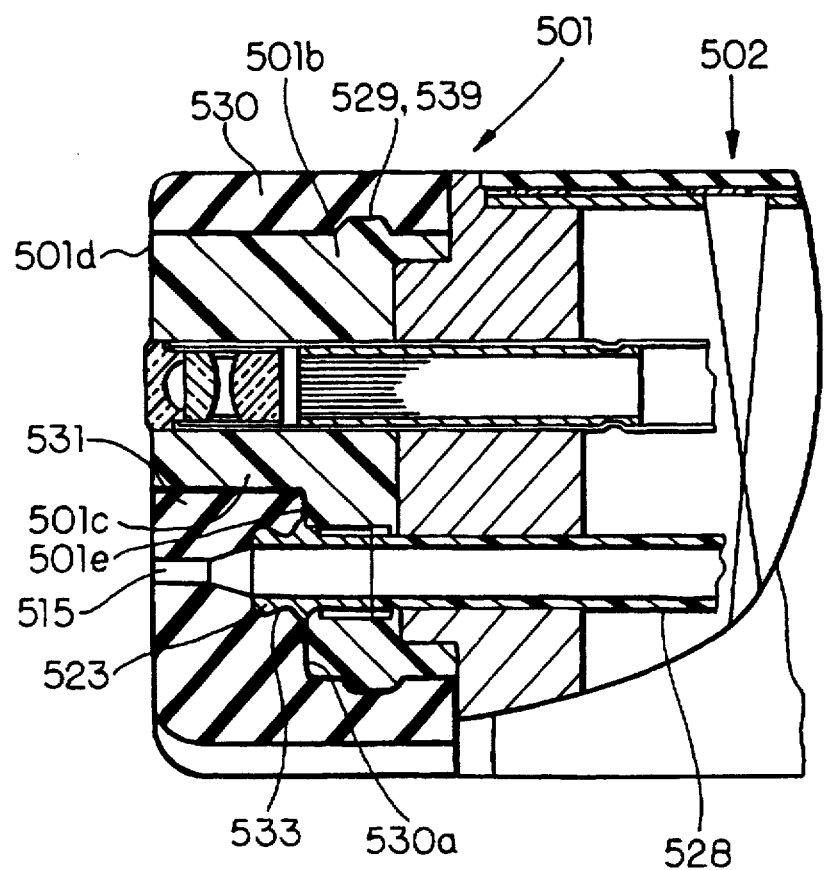
FIG. 10 is a longitudinal sectional view taken along the line A-B-E-F in FIG. 11, in which an end cap is attached to a front end body according to a fifth embodiment of the present invention.
Figure 11:
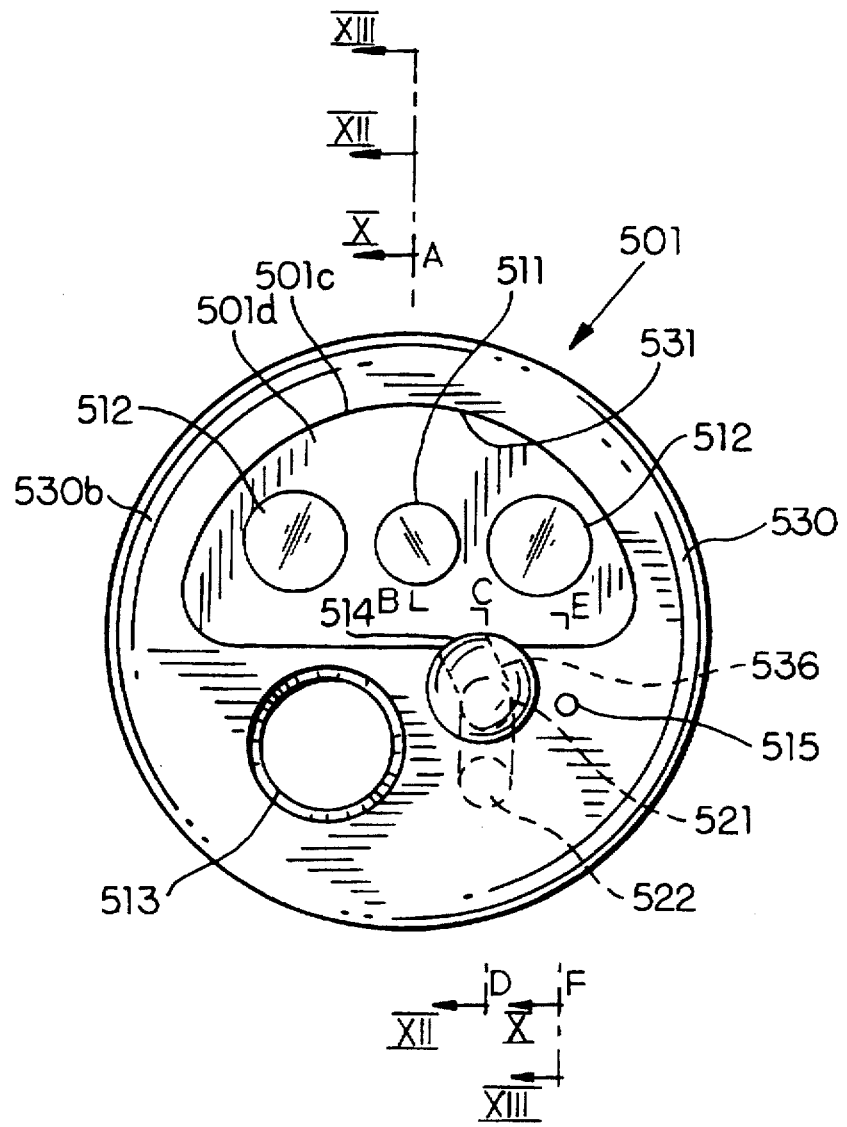
FIG. 11 is a front elevational view of a front end structure of an endoscope having an end cap attached to a front end body, according to a fifth embodiment of the present invention.
Figure 12:
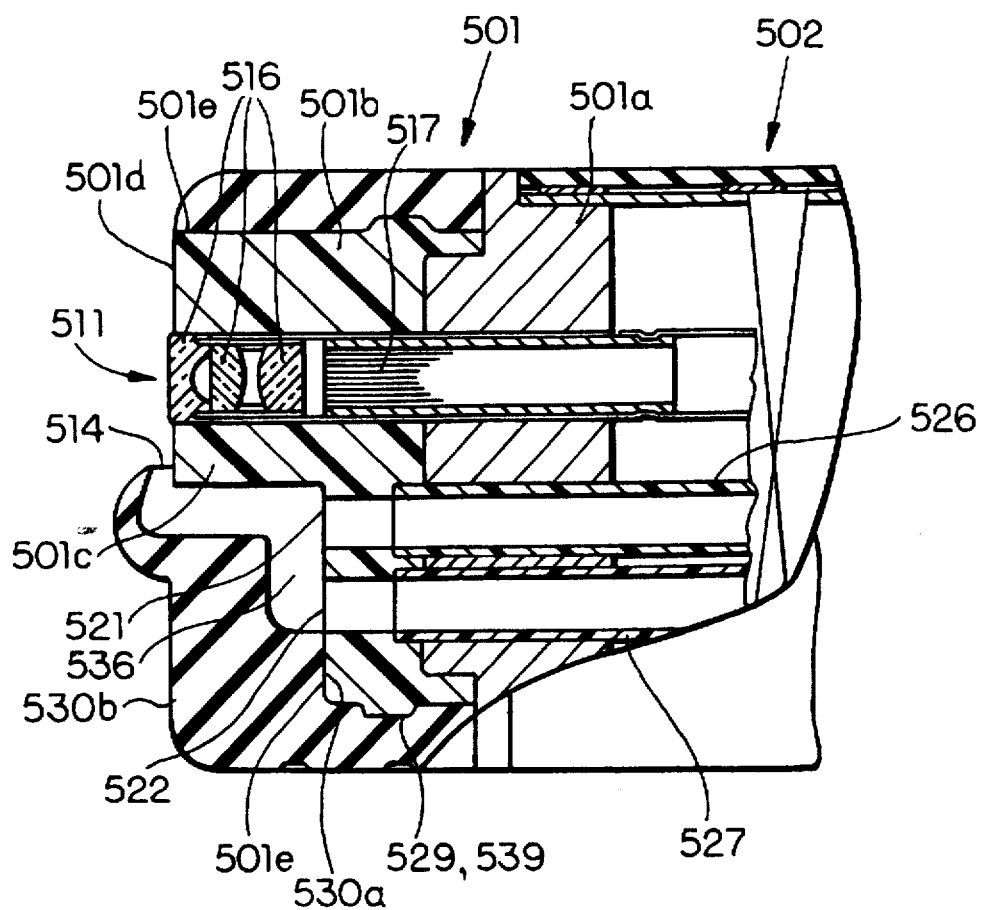
FIG. 12 is a side sectional view of a front end structure of an endoscope having an end cap attached to a front end body, according to a fifth embodiment of the present invention.
Figure 13:
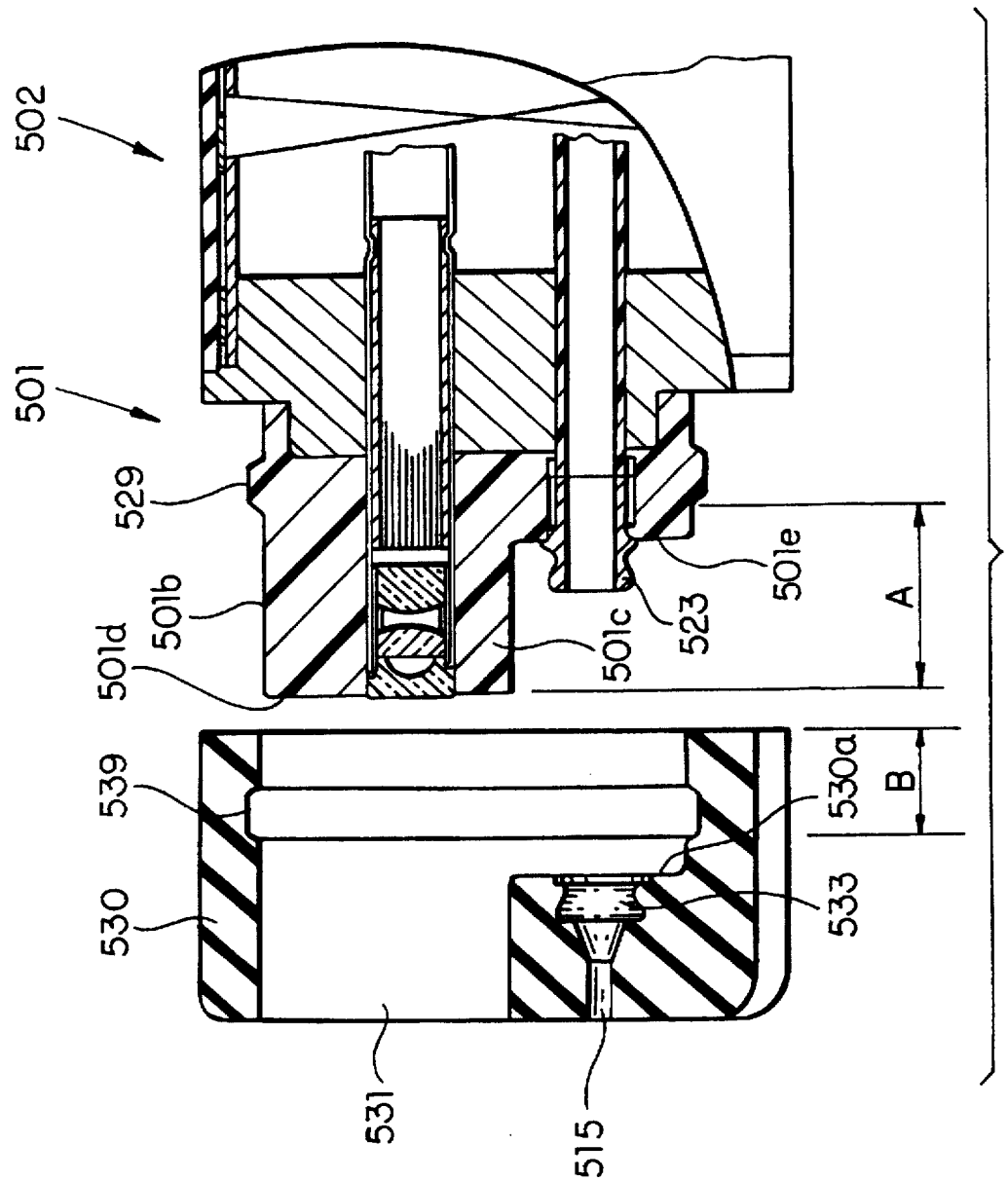
FIG. 13 is a side sectional view of a front end structure of an endoscope in which an end cap is detached from a front end body, according to a fifth embodiment of the present invention.
Figure 14:
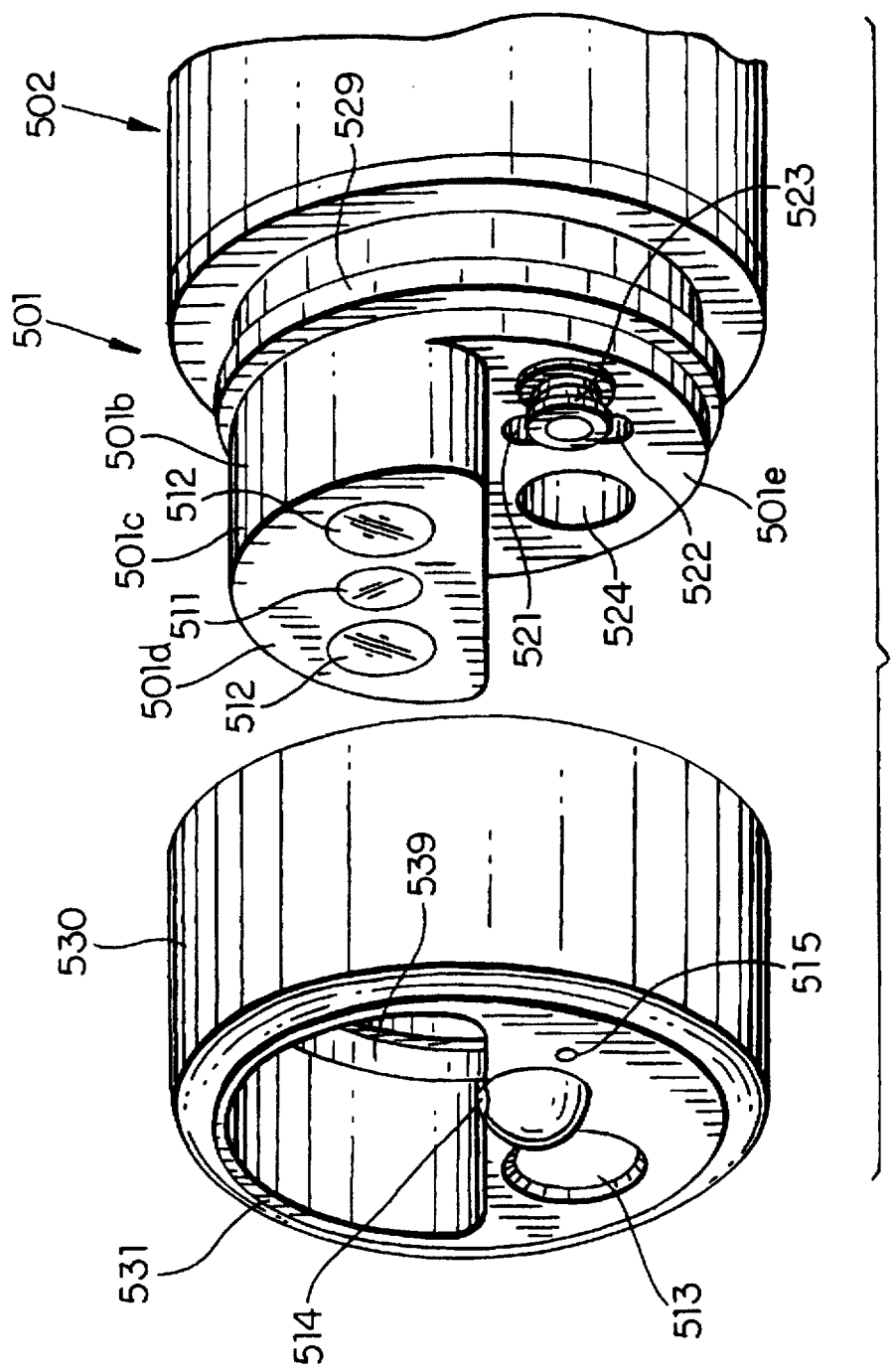
FIG. 14 is a perspective view of a front end structure of an endoscope in which an end cap is detached from a front end body, according to a fifth embodiment of the present invention.
Figure 15:
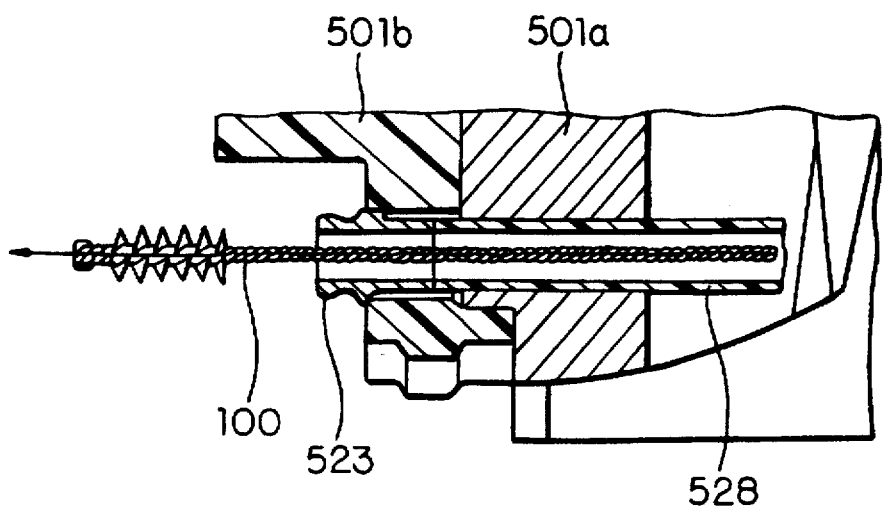
FIG. 15 is a partial sectional view of a front end structure to explain the cleaning operation, according to a fifth embodiment of the present invention.

FIGS. 10 through 16 show a fifth embodiment of the present invention. FIG. 11 is a front elevational view of a front end of an endoscope to which an end cap is attached, and FIG. 10 is a sectional view taken along the line A-B-E-F in FIG. 11. FIG. 12 is a sectional view taken along the line A-B-C-D in FIG. 11. FIG. 13 is a sectional view taken along the line A-B-E-F in FIG. 11, in which the end cap is detached from the front end body, and FIG. 14 is a perspective view of FIG. 13.

As can be seen in FIG. 12, a front end body 501 is connected to a front end of a flexable portion 502 which is provided on the front end of an inserting portion in the form of an elongated flexible tube so as to bend in accordance with a remote control operation.

The front end body 501 is provided with a metal block portion 501a connected to the flexible portion 502, and a plastic portion 501b secured to the front end of the metal block portion 501a to form an integral assembly.

In the illustrated embodiment, the endoscope is a forward view type endoscope to view the forward direction of the longitudinal axis. As shown in FIG. 11, the front end body 501 is provided on the front end surface thereof with a viewing window 511 and illuminating windows 512. The end cap 530 is provided with a forceps channel outlet hole 513, an air/water injection nozzle 514 which opens toward the viewing window 511, and a jet flow injection nozzle 515 which opens in the viewing direction.

In a passage connected to the viewing window 511, there are an objective optical system 516 and an image receiving end of an image guiding fiber bundle 517, as shown in FIGS. 10, 12 and 13. There is an emitting end of a light guiding fiber bundle (not shown) in a passage connected to the illuminating windows 512. Note that the present invention can be applied to an electronic endoscope using a solid state image sensor which transmits an image represented by electric signals, or rigid endoscope, etc.

As can be seen, for example, in FIG. 14, the front end of the plastic portion 501b of the front end body 501 is provided on an end surface 501e thereof with a projection 501c which is formed by partially projecting the portion of the front end of the plastic portion 501b from the end surface 501e that includes the viewing window 511 and the illuminating windows 512. Namely, the viewing window 511 and the illuminating windows 512 are provided in the projection 501c. The projection 501c has a semicircular cross section.

The viewing window 511 and the illuminating windows 512 (outer surfaces of the glass covers thereof) are flush with the outer end surface (projecting end surface) 501d of the projection 501c. The end surface 501e is provided with an air discharge port (air supply port) 521, a water discharge port (water supply port) 522, and a forceps channel opening 524. Note numeral 523 designates a connecting pipe connected to a jet flow injecting water supply port 523.

The connecting pipe 523 is screwed, at the base end thereof, in the jet flow injecting water discharge port of the plastic portion 501b, as can be seen in FIG. 13. The connecting pipe 523 is connected to the jet flow injecting water feed tube 528. The inner diameter of the connecting pipe 523 is identical to the inner diameter of the water feed tube 528.

The outer end of the connecting pipe 523 has an outer diameter which gradually increases toward the outer end thereof and is rounded at the end edges thereof.

The air supply port 521 and the water supply port 522 are respectively connected to an air feed tube 526 and a water feed tube 527, inserted in and connected to the front end body 501 from the rearward direction, as may be seen in FIG. 12. Similarly, the jet flow injecting water supply port 523 and the forceps channel opening 524 are respectively connected to a jet flow injecting water feed tube and a forceps channel (not shown).

A substantially cylindrical end cap 530 which is made of an elastic material, such as rubber is detachably attached to the outer peripheral surface of the front end of the plastic portion 501b of the front end body 501. The diameter and shape of the inner peripheral surface of the end cap 530 are substantially identical to those of the outer peripheral surface of the front end body 501.

The end cap 530 has an outer diameter identical to that of the front end body 501 and is shaped such that an intermediate surface 530a thereof comes into close contact with the front end surface 501e of the front end body 501 and that the outer surface (front surface) 530b of the end cap 530 is substantially flush with the projecting end surface 501d of the projection 501c, except for the hemispherical nozzle portion defining the nozzle 514.

The end cap 530 is provided with a semicircular insertion hole 531 whose shape and diameter correspond to those of the projection 501c having a semicircular shape in cross section, so that when the end cap 530 is attached to the front end body 501, the projection 501c can be fitted in the insertion hole 531 to determine the relative angular position therebetween in the rotational direction.

As shown in FIGS. 11 and 12, the end cap 530 is provided on the rear surface thereof with a nozzle passage 536 in the form of a recessed groove, which is connected in a liquid-tight state to the air feed port 521 and the water feed port 522 when the end cap 530 is attached to the front end body 501. The outlet end of the nozzle passage 536 defines the nozzle 514 which opens into the surface of the viewing window 511.

Moreover, the end cap 530 is provided on the intermediate surface 530a thereof with a connecting hole 533 corresponding to a connecting pipe 523 which extends through the end surface 501e of the plastic portion 501b to be connected to the jet flow injecting water feed tube 528, so that the connecting pipe 523 can be fitted in the connecting hole 533. The jet flow injecting nozzle 515 having a small diameter is linearly connected to the connecting hole 533.

The shape and size of the inner peripheral surface of the connecting hole 533 are substantially identical to those of the outer surface of the projection portion of the connecting pipe 523.

When connected and when water is sent forth from the jet flow injecting water feed tube 528, water does not leak from the junction of the connecting pipe 523 and connecting hole 533.

Accordingly, water sent forth from the jet flow injecting water feed tube 528 is outputted from the nozzle 515 and washes away filth stuck to objective portion.

As can be seen in FIGS. 10, 12, 13 and 14, the plastic portion 501b of the front end body 501 is provided on the outer peripheral surface with a peripheral projection 529 which is located behind the end surface 501e. The end cap 530 is provided on the inner peripheral surface thereof with a peripheral groove 539 whose diameter and shape are substantially identical to those of the projection 529, so that the projection 529 can be fitted in the recessed groove 539.

Consequently, when the projection 529 is fitted in the groove 539, the end cap 530 is connected to the front end body 501 so as not to be accidentally detached from the front end body 501. To detach the end cap 530 from the front end body 501, a force large enough to elastically deform the end cap 530 must be applied to the end cap 530.

As shown in FIG. 13, assuming that the length of the front end body 501 from the front end surface 501d to the projection 529 is "A", and the length of the end cap 530 from the rear end surface thereof to the intermediate surface 530a which defines an inlet end of the insertion hole 531 is "B", A is larger than B (i.e., A>B).

Figure 16:
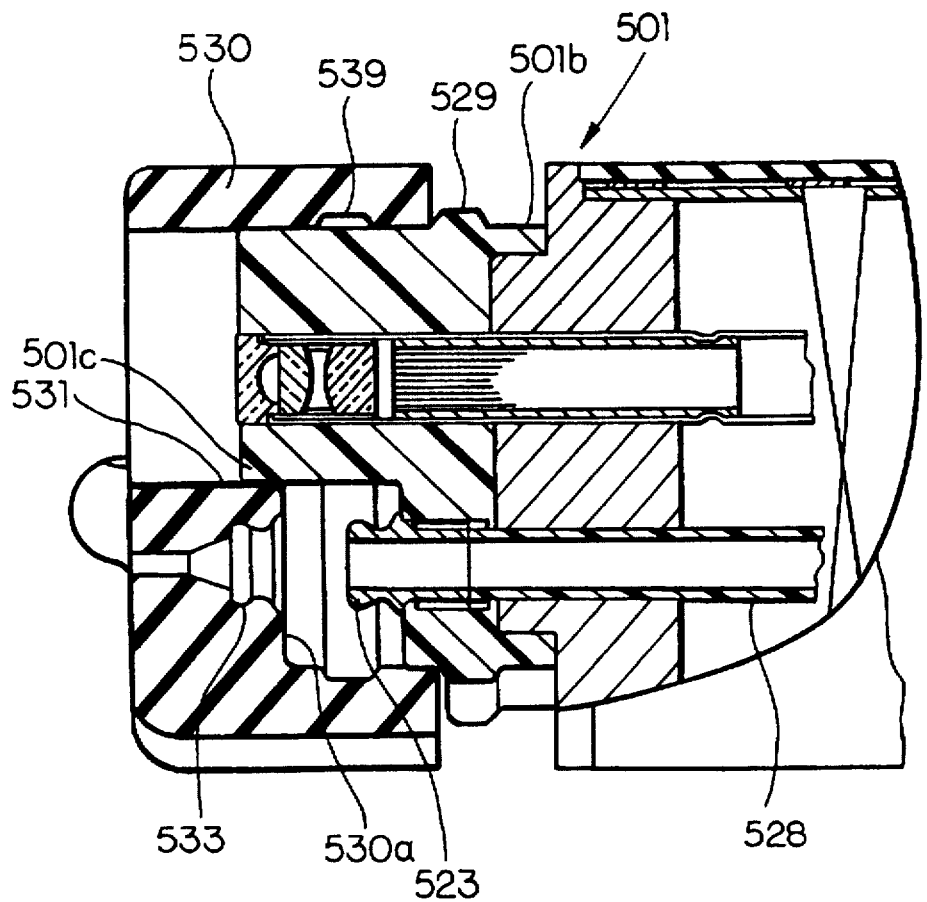
FIG. 16 is a side sectional view of a front end structure of an endoscope having an end cap which is being attached to a front end body, according to a fifth embodiment of the present invention.

Consequently, when the end cap 530 is fitted on the outer peripheral surface of the front end body 501 from the front end of the latter, the front end of the projection 501c of the front end body 501 is inserted in the insertion hole 531 of the end cap 530 before the rear end of the end cap 530 reaches the projection 529, as shown in FIG. 16.

As can be seen in FIG. 16, no elastic deformation of the end cap 530 occurs before the rear end of the end cap 530 rides over the projection 529. Therefore, when the relative rotation takes place between the end cap 530 and the front end body 501 to fit the projection 501c in the insertion hole 531, there is no or little frictional resistance therebetween, and hence, easy rotation and positioning can be achieved.

When the end cap 530 is moved in the axial direction of the front end body 501 in a state shown in FIG. 16 upon completion of the relative angular position, the rear end of the end cap 530 rides over the projection 529, so that the projection 529 can be fitted in the recess 539 to establish a firm connection of the end cap 530 with the front end body 501.

The end cap 530 is detached from the front end body 501 after the endoscope is used to allow the cleaning of the jet flow injecting water feed tube 528 and the connecting pipe 523, using a cleaning brush which is inserted in the jet flow injecting water feed tube 528 and the connecting pipe 523 and pushed through the entire length thereof. The air feed tube 526 and the water feed tube 527 can be also be cleaned using a cleaning brush.

Figure 17:
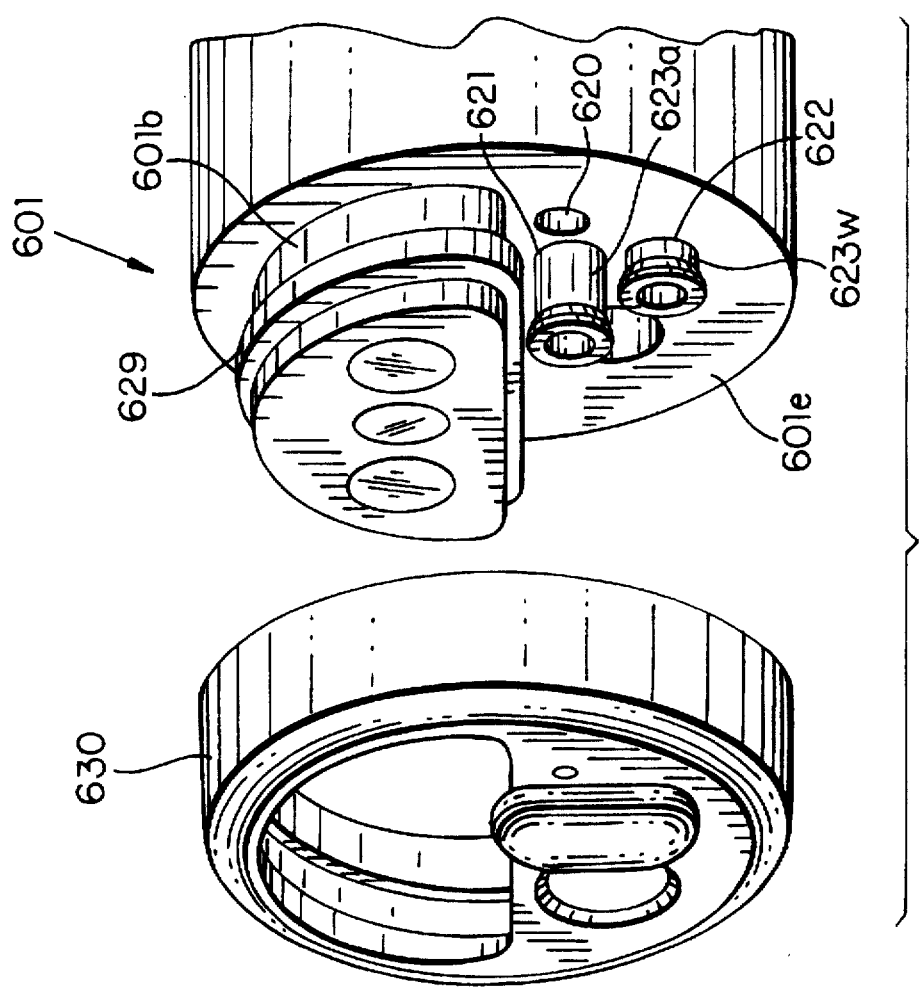
FIG. 17 is a perspective view of a front end body and an end cap detached therefrom, according to a sixth embodiment of the present invention.

FIG. 17 shows a sixth embodiment of the present invention, in which the air discharge port (air supply port) 621 and the water discharge port (water supply port) 622 are provided with connecting pipes 623a and 623w, similar to the connecting pipe 623 in the fifth embodiment. Numeral 620 designates the jet flow injecting water discharge port. The end cap 630 is provided with connecting holes (not shown) corresponding to the connecting pipes 623a and 623w to receive the same. With this arrangement, no leakage of the air and water occurs.

In the sixth embodiment, the connecting pipes 623a and 623w have different projection lengths for the purpose of an easy insertion and removal of the connecting pipes 623a and 623w in and from the associated connecting holes. Alternatively, it is possible to provide the connecting pipe in all of the air discharge port 621, the water discharge port 622 and the jet flow injecting water discharge port 620.

Figure 18:
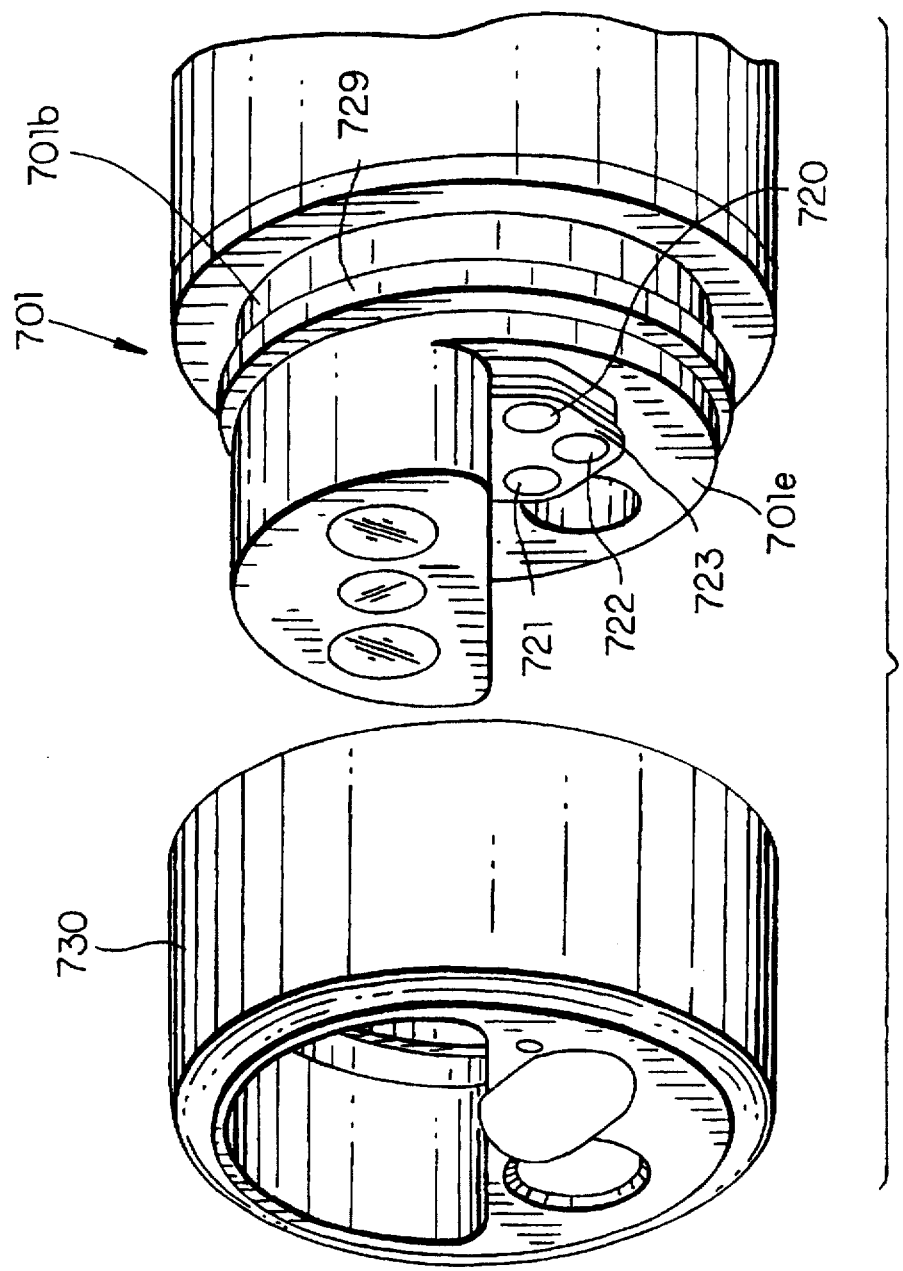
FIG. 18 is a perspective view of a front end body and an end cap detached therefrom, according to a seventh embodiment of the present invention.

FIG. 18 shows a seventh embodiment of the present invention. In the seventh embodiment, the air discharge port 721, the water discharge port 722 and the jet flow injecting water discharge port 720 are formed in a connecting projection 723 which is provided on the end surface 701e of the front end of the front end body 701. The end cap 730 is provided with a connecting hole (not shown) corresponding to the connecting projection 723.

As can be understood from the foregoing, according to the present invention, since the connecting pipe projecting from the front end body is fitted in the connecting hole formed in the end cap to establish a fluid connection therebetween when the end cap is attached to the front end body of the endoscope, there is no air or water leakage at the connection, so that the viewing window and the illuminating windows can be well cleaned so as to obtain a clear image of an object to be viewed.

Figure 19:
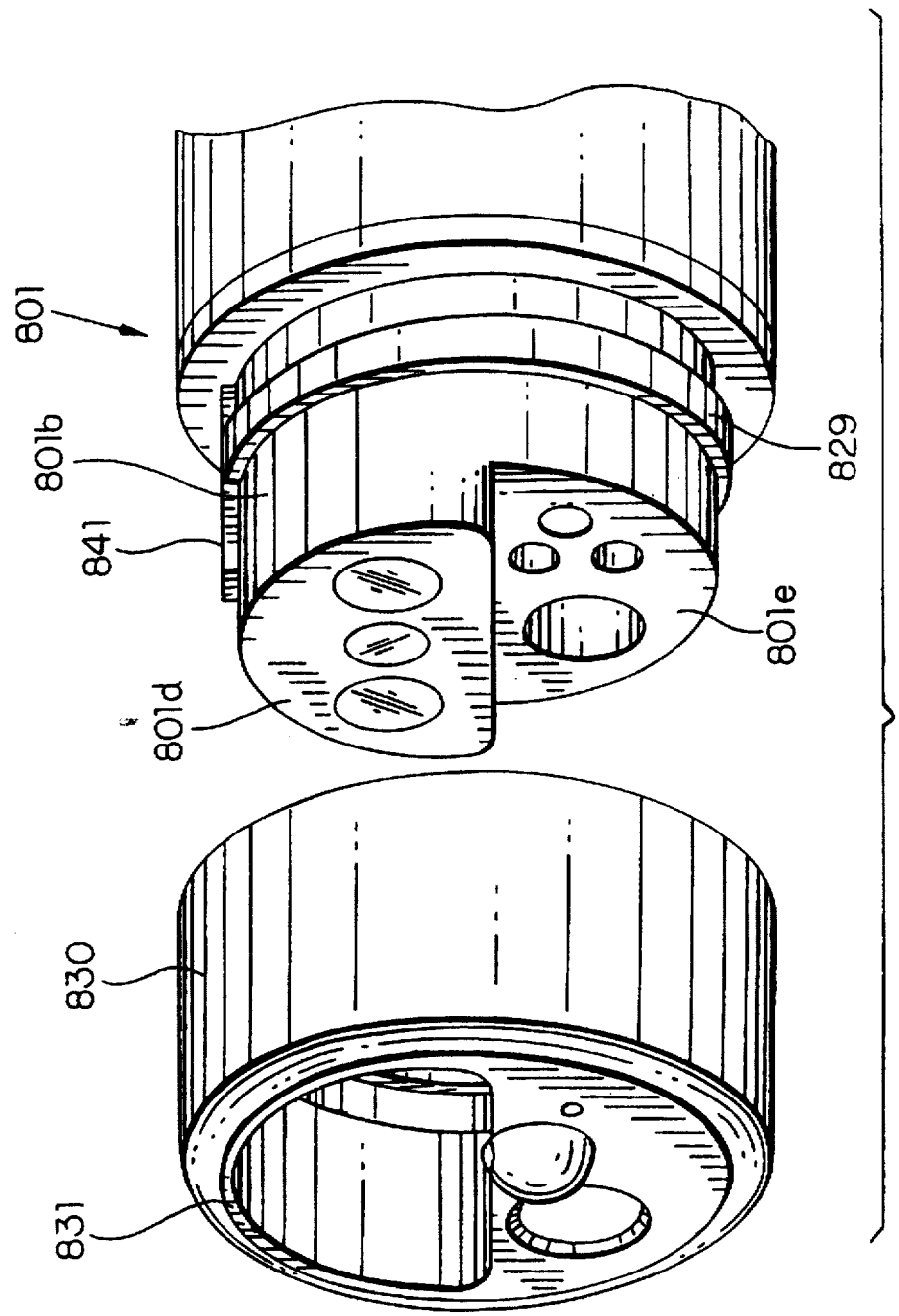
FIG. 19 is a perspective view of a front end structure of an endoscope in which an end cap is detached from a front end body, according to a eighth embodiment of the present invention.
Figure 20:
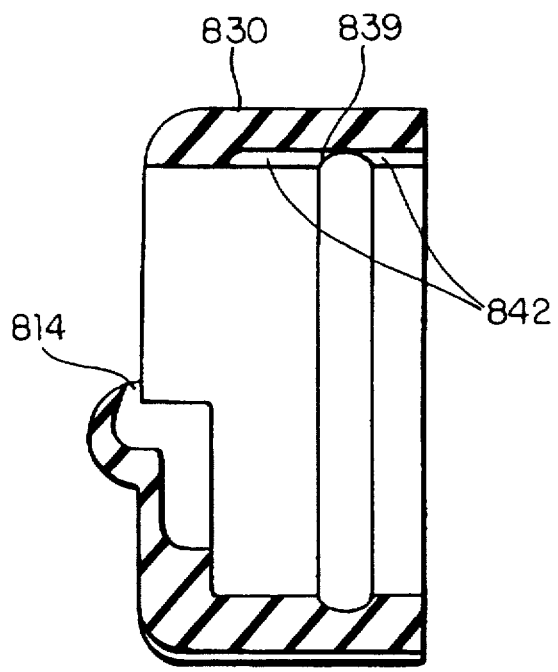
FIG. 20 is a side sectional view of an end cap according to a eighth embodiment of the present invention.
Figure 21:
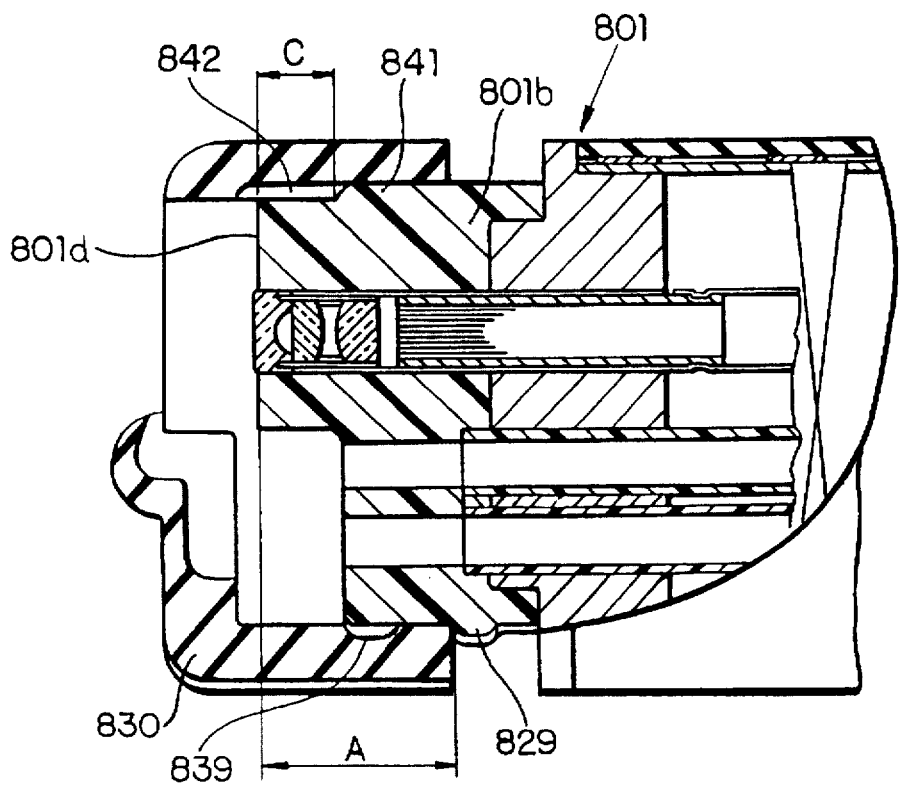
FIG. 21 is a side sectional view of a front end structure of an endoscope having an end cap which is being attached to a front end body, according to a eighth embodiment of the present invention.

FIGS. 19 through 21 show an eighth embodiment of the present invention. FIG. 19 shows a perspective view of a front end structure of an endoscope in which the end cap is detached from the front end body; FIG. 20 shows a side sectional view of the end cap 830; and FIG. 21 shows a side sectional view of a front end structure of an endoscope wherein the end cap is being attached to the front end body 801, respectively.

In the eighth embodiment, the front end body 801 is provided, on the outer peripheral surface of the plastic portion 801b, with a positioning projection 841 which extends in the axial direction thereof, and the end cap 830 is provided on the inner peripheral surface thereof with a positioning recess 842 which extends in the axial direction, so that the positioning projection 841 can be engaged in the positioning recess 842.

The recess 842 opens into the rear end surface of the end cap 830. The positioning projection 841 which fits into the positioning recess 842 to ensure the correct relative angular position between the front end body 801 and the end cap 830 in the rotational direction is located closer to the front end surface 801d of the front end body 801 than the projection 829 which is adapted to prevent the end cap from being accidentally detached from the front end body 801. Namely, A>C in FIG. 21.

In the eighth embodiment, upon attaching the end cap 830 to the front end body 801, since the positioning projection 841 is fitted in the recess 842 before an elastic deformation of the end cap 830 takes place when the rear end of the end cap 830 rides over the accidental disengagement preventing projection 829, the determination of the relative angular position between the end cap 830 and the front end body 801 can be easily executed with no or little frictional resistance therebetween.

Figure 22:
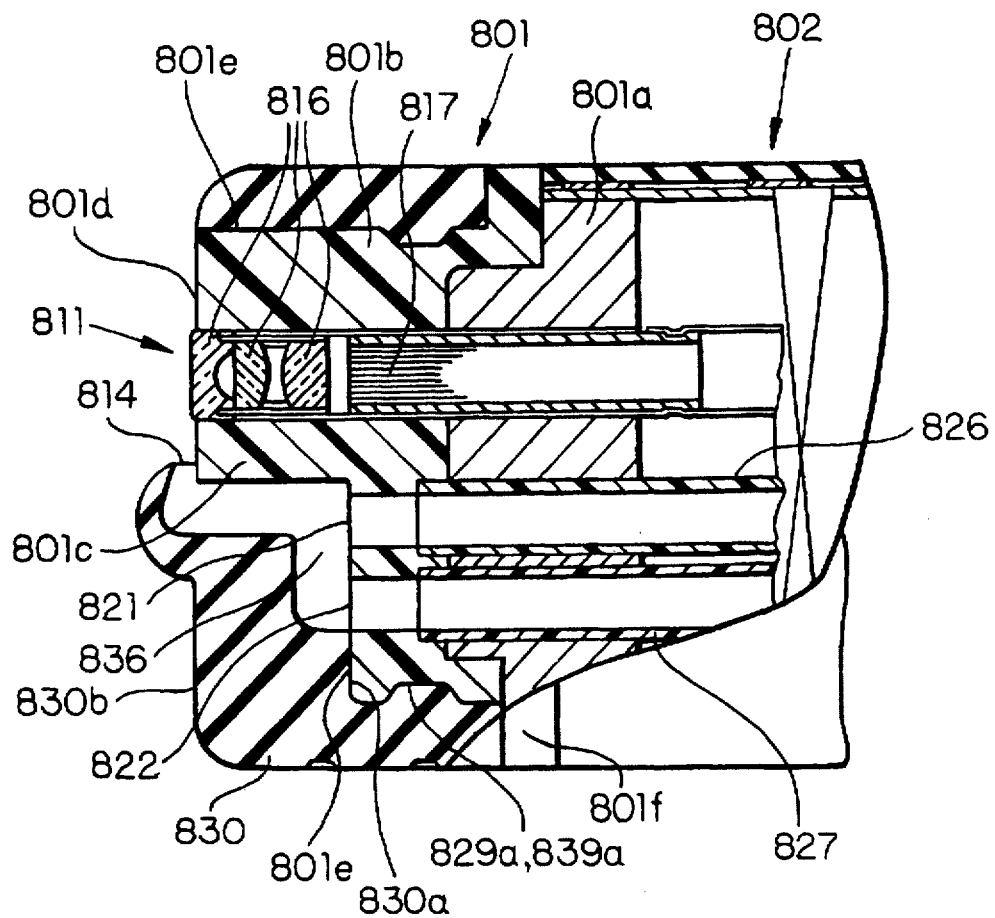
FIG. 22 is a perspective view of a front end body and an end cap detached therefrom, according to a eighth embodiment of the present invention.
Figure 23:
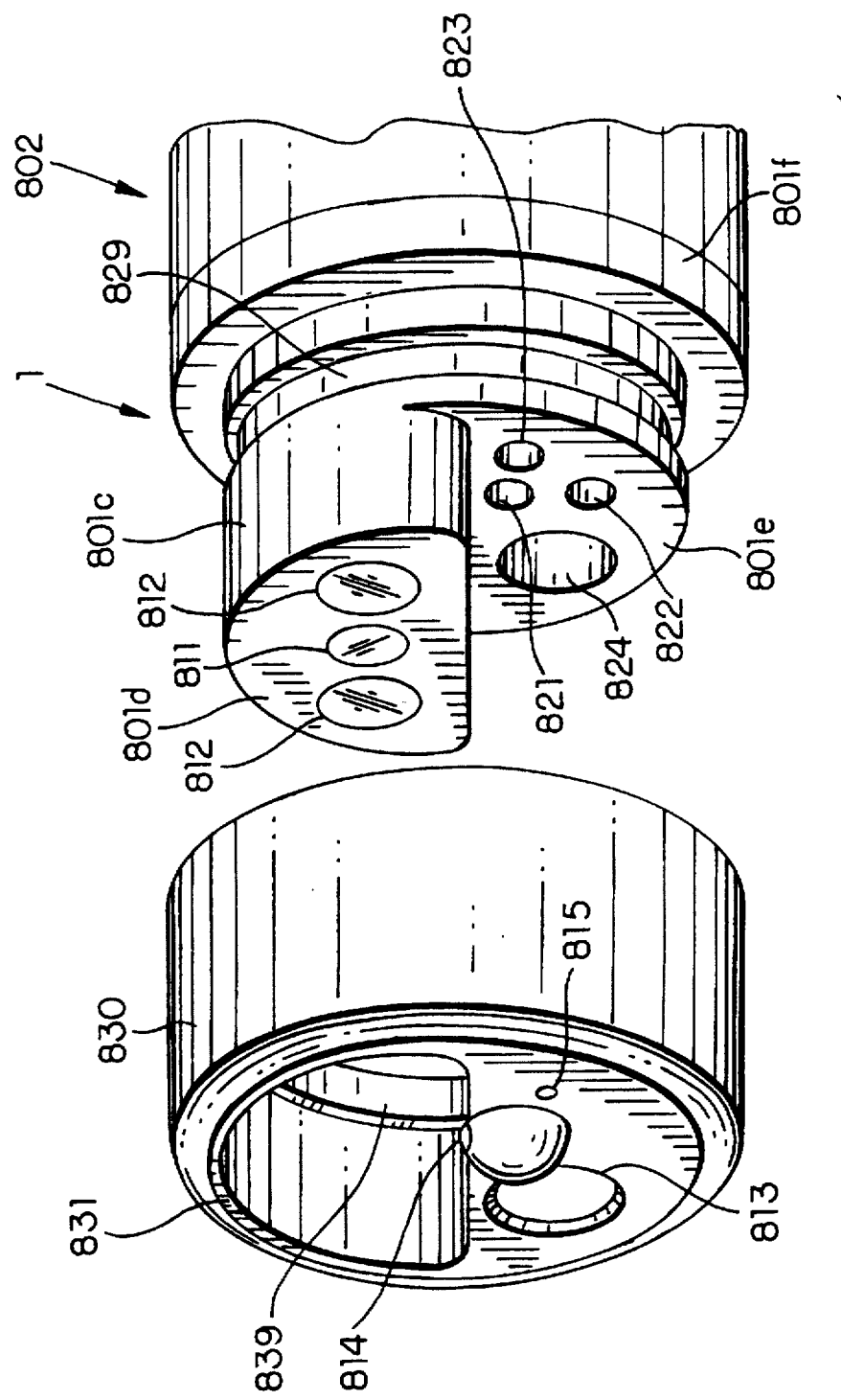
FIG. 23 is a perspective view of a front end body and an end cap detached therefrom, according to a eighth embodiment of the present invention.

In the eighth embodiment, alternatively the end cap 830 can be provided with a projection 829a and the the plastic portion 801b can be has a groove 839a as shown in FIGS. 22 and 23.

Figure 24:
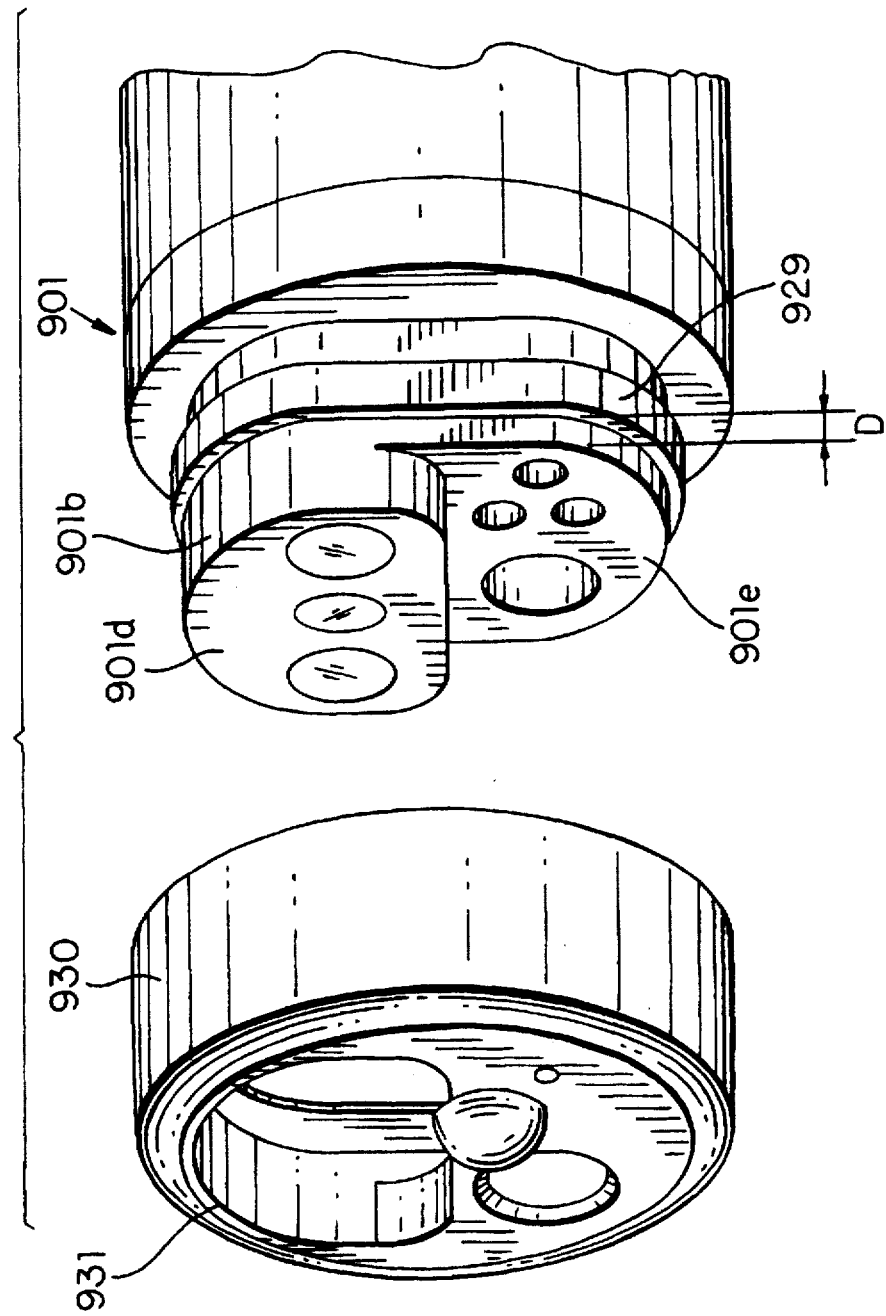
FIG. 24 is a perspective view of a front end structure of an endoscope in which an end cap is detached from a front end body, according to a ninth embodiment of the present invention.

FIG. 24 shows a ninth embodiment of the present invention, in which the plastic portion 901b of the front end body 901 is of a non-circular shape and is elongated-circular or oval shape in the illustrated embodiment. The inner surface of the end cap 930 corresponds to the shape of the plastic portion 901b so as to carry out the positioning between the end cap and the front end body in the rotational direction.

In the ninth embodiment, the projection 929 is provided on the outer peripheral surface of the oval plastic portion 901b. Since the value of D in FIG. 22 is always a positive value (D>0), the positioning in the rotational direction is carried out by the engagement of the oval projection 929 and the oval inner surface of the end cap 930 before the end cap 930 reaches the projection 929, so that the positioning can be easily effected by a small external force owing to an absence of a frictional resistance.

Note that the basic structures of the eighth and ninth embodiments are the same as that of the first embodiment except for the presence or absence of the connecting pipe in the jet flow injecting passage, and accordingly, no detailed explanation therefor will be given herein.

As can be understood from the foregoing, according to the present invention, since the positioning of the relative angular position between the end cap and the front end body is effected by the positioning means before the elastic deformation of the end cap takes place to engage the accidental disconnection preventing projection in the accidental disconnection preventing recess, there is no or little frictional resistance during the relative rotation of the end cap and the front end body. Hence, no excess force is applied to the front end of the endoscope upon attachment of the end cap to the front end body, thus resulting in an easy attachment of the end cap to the endoscope without a fear of breakage thereof.

FIGS. 25 through 31 show a tenth embodiment of the present invention.

Figure 25:
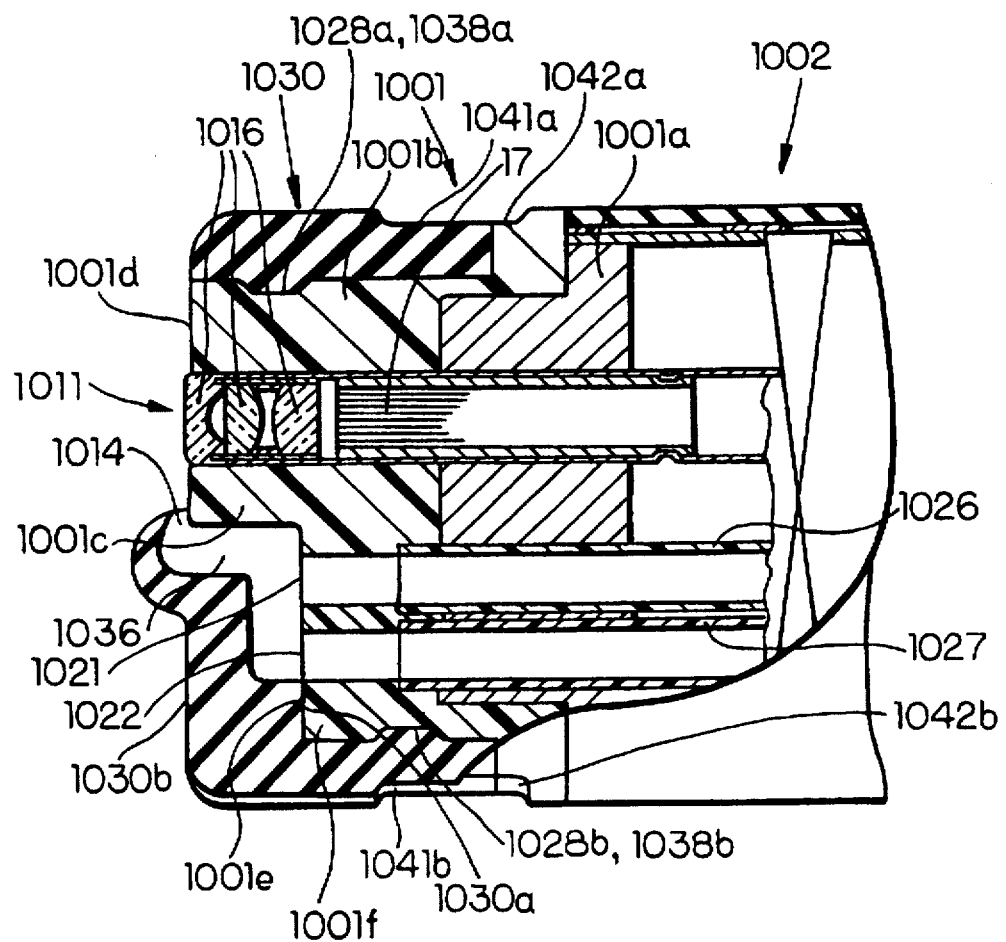
FIG. 25 is a sectional view taken along the line A-B-C-D in FIG. 26, according to an tenth embodiment of the present invention.
Figure 26:
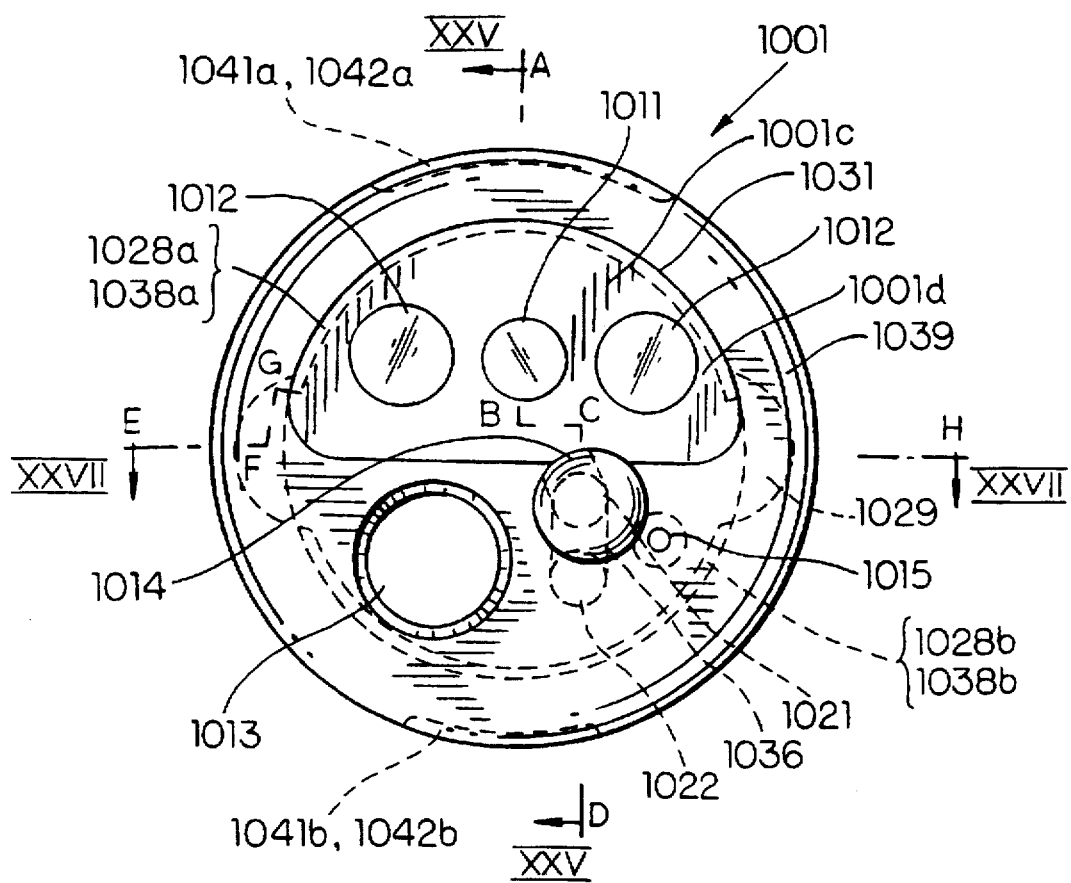
FIG. 26 is a front elevational view of FIG. 25.
Figure 27:
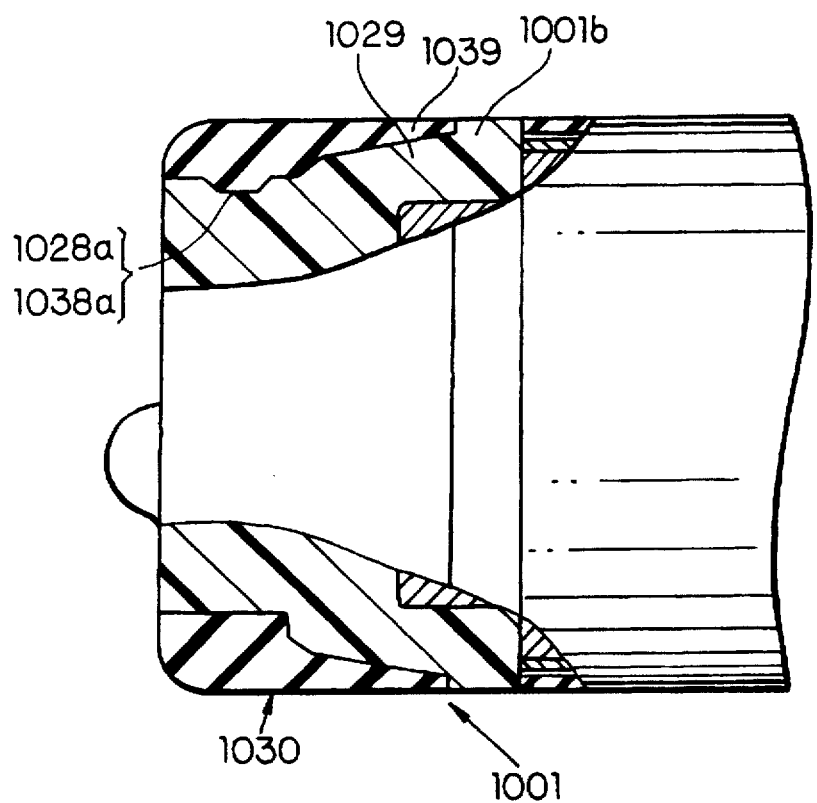
FIG. 27 is a sectional view taken along the line E-F-G-B-H in FIG. 26.
Figure 28:
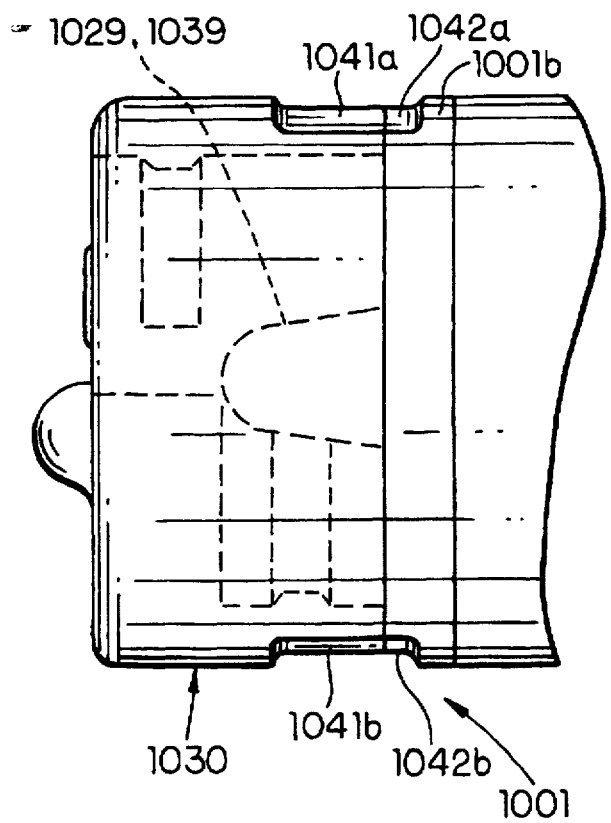
FIG. 28 is a side elevational view of FIG. 25.
Figure 29:
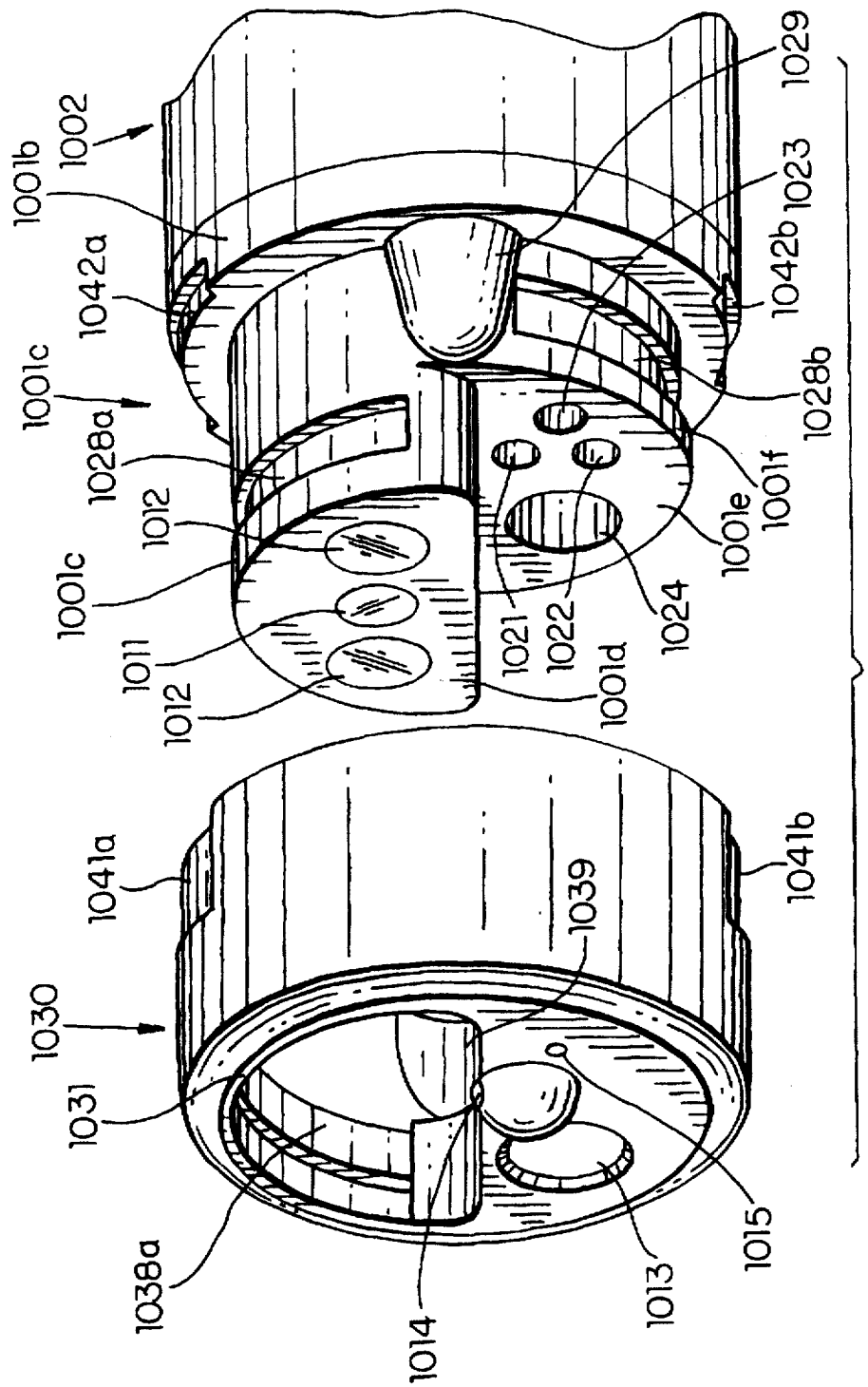
FIG. 29 is a perspective view of a front end body of an endoscope and an end cap detached from the front end body.

FIG. 26 shows a front elevational view of a front end body of an endoscope; FIG. 25 is a sectional view taken along the line A-B-C-D in FIG. 26; FIG. 27 is a sectional view taken along the line E-F-G-B-H in FIG. 26; FIG. 28 is a side elevational view of FIG. 25; and, FIG. 29 is a perspective view of a front end body of an endoscope and an end cap detached from the front end body.

As can be seen in FIG. 25, the front end body 1001 is connected to a front end of a flexable portion 1002 which is provided on the front end of an inserting portion in the form of an elongated flexible tube so as to bend in accordance with a remote control operation.

The front end body 1001 is provided with a metal block portion 1001a connected to the flexable portion 1002, and a plastic portion 1001b secured to the front end of the block portion 1001a to form an integral assembly.

In the illustrated embodiment, the endoscope is a forward view type endoscope to view the forward direction of the longitudinal axis. The front end body 1001 is provided on the front end surface thereof with a viewing window 1011 and illuminating windows 1012, as shown in FIG. 26. The end cap 1030 is provided with a forceps channel outlet hole 1013, an air/water injection nozzle 1014 which opens toward the viewing window 1011, and a jet flow injection nozzle 1015 which opens in the viewing direction.

In a passage connected to the viewing window 1011, there is an objective optical system 1016 and an image receiving end of an image guiding fiber bundle 1017, as shown in FIG. 27. There is an emitting end of a light guiding fiber bundle (not shown) in a passage connected to the illuminating windows 1012.

As can be seen, for example, in FIG. 29, the front end of the plastic portion 1001b of the front end body 1001 is provided on an end surface 1001e thereof with a projection 1001c which is formed by partially projecting the portion of the front end of the plastic portion 1001b from the end surface 1001e that includes the viewing window 1011 and the illuminating windows 1012. Namely, the viewing window 1011 and the illuminating windows 1012 are provided in the projection 1001c. The projection 1001c has a semi-circular cross section and is located on an upper half of the end surface 1001e.

The end surface 1001e is provided with an air discharge port (air supply port) 1021, a water discharge port (water supply port) 1022, a jet flow injecting water supply port 1023 and a forceps channel opening 1024.

The air supply port 1021 and the water supply port 1022 are respectively connected to an air feed tube 1026 and a water feed tube 1027, inserted in and connected to the front end body 1001 from the rearward direction, as may be seen in FIG. 25. Similarly, the jet flow injecting water supply port 1023 and the forceps channel opening 1024 are respectively connected to a jet flow injecting water feed tube (not shown) and a forceps channel (not shown).

The substantially cylindrical end cap 1030 which is made of an elastic material, such as rubber is detachably attached to the outer peripheral surface of the front end of the plastic portion 1001b of the front end body 1001. The shape and diameter of the inner peripheral surface of the end cap 1030 are substantially identical to those of the outer peripheral surface of the front end body 1001.

The end cap 1030 has an outer diameter identical to that of the front end body 1001 and is shaped such that the annular end surface 1030a thereof comes into close contact with the front end surface 1001e of the front end body 1001 and that the outer surface (front surface) of the end cap 1030 is substantially flush with the projecting end surface 1001d of the projection 1001c, except for the hemispherical nozzle portion defining the nozzle 1014.

The end cap 1030 is provided with an insertion hole 1031 whose shape corresponds to the projection 1001c having a semicircular shape in cross section, so that when the end cap 1030 is attached to the front end body 1001, the projection 1001c can be fitted in the insertion hole 1031 to determine the relative angular position therebetween.

As shown in FIGS. 25 and 26, the end cap 1030 is provided on the rear surface thereof with a nozzle passage 1036 in the form of a recessed groove, which is connected in a liquid-tight state to the air feed port 1021 and the water feed port 1022 when the end cap 1030 is attached to the front end body 1001. The outlet end of the nozzle passage 1036 defines the nozzle 1014 which opens into the outer surface of the viewing window 1011.

As may be seen in FIGS. 25 and 25, the projection 1001c of the front end body 1001 is provided on the outer peripheral surface thereof with a circumferentially extending first recess 1028a which is adapted to prevent the end cap from being accidentally disengaged from the front end body 1001. A second recess 1028b which is adapted to prevent the end cap from being accidentally disengaged from the front end body 1001 is provided on the lower half of the outer peripheral surface of the cylindrical portion 1001f (i.e., located behind the end surface 1001e of the front end portion) which constitutes the base portion for the projection 1001c. Namely, the second recess 1028b is offset in the axial direction of the front end body 1001 from the first recess 1028a.

The end cap 1030 is provided on the inner peripheral surface thereof with first and second projections 1038a and 1038b which radially and inwardly project to be fitted in the corresponding first and second recesses 1028a and 1028b, so that when the end cap 1030 is attached to the front end body 1001, the first and second projections 1038a and 1038b are fitted in the first and second recesses 1028a and 1028b to prevent the end cap from being accidentally disconnected from the front end body to thereby firmly connect the end cap to the front end body.

Thus, the engagement between the first projection 1038a and the first recess 1028a and between the second projection 1038b and the second recess 1028b ensures that the end cap 1030 is firmly connected to the front end body 1001 so as not to be accidentally disengaged therefrom. To disconnect the end cap 1030 from the front end body 1001, it is necessary to exert a relatively strong force on the end cap to elastically deform the same.

As shown in FIGS. 26, 27 and 28, the end cap 1030 is provided, on the rear half thereof in the axial direction, with right and left thin portions (semicircular recesses in cross section) 1039, so that the end cap 1030 can be easily bent in the radial direction at the reduced thickness portions 1039. The front end body 1001 is provided with ridged portions 1029 which can be fitted in the reduced thickness portions 1039 adjacent to the thin portions 1039. The ridged portions 1029 can be dispensed with.

There are marks (recesses 1041a, 1041b and 1042a, 1042b) 1041 and 1042 which serve as a sign to indicate the direction in which an external force is to be applied to attach or detach the end cap 1030, on the end cap 1030 and the front end body 1001, respectively. The marks 1041 and 1042 are visible from the outside, so that the relative angular position between the end cap and the front end body can be certainly and visually carried out.

Consequently, the portion to which an optimum external force is to be applied can be easily and visually confirmed upon attachment or detachment of the end cap to and from the front end body. Thus, there is no fear that the front end body 1001 is broken by a strong force which would be otherwise applied thereto. Preferably, the upper marks 1041a, 1042a and the lower marks 1041b and 1042b have different widths (or lengths), so that there is no possibility that the end cap is attached to the front end body at a wrong angular position by 180°.

Figure 30:
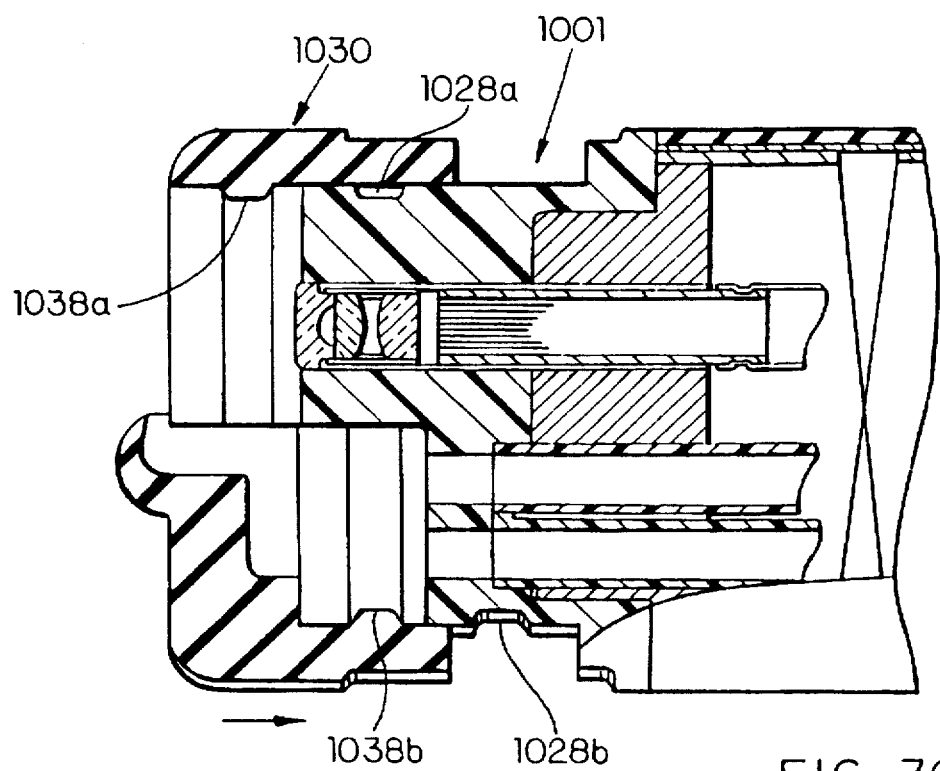
FIG. 30 is a side sectional view of a front end body of an endoscope and an end cap which is being detached from the front end body.
Figure 31:
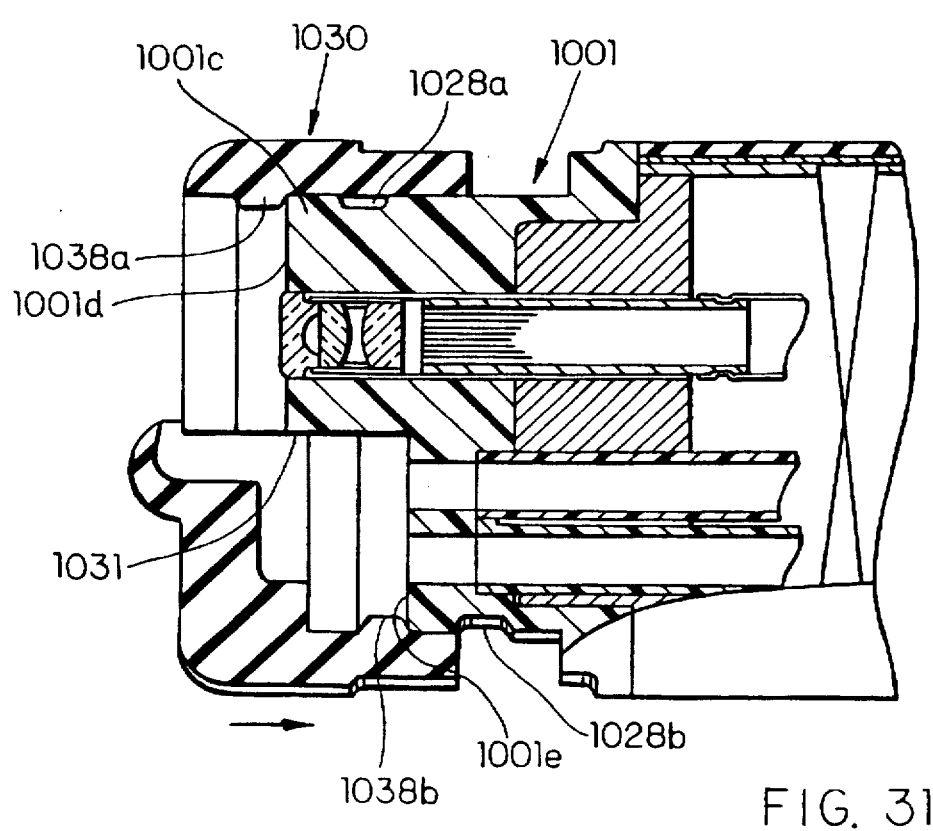
FIG. 31 is a side sectional view of a front end body of an endoscope and an end cap which is being detached from the front end body; and, FIGS. 32A, 32B, 32C, 32D are schematic side elevational view of four different kinds of endoscopes and end caps, according to an embodiment of the present invention.

In different transition positions shown in FIGS. 30 and 31, the end cap 1030 is being attached to the front end body 1001 from the front end side thereof. In FIG. 30, the front end body 1001 is inserted in the end cap 1030 so that the outer peripheral surface of the front end body 1001 is in close surface contact with the inner peripheral surface of the end cap 1030.

When a further insertion of the front end body in the end cap 1001 takes place, the projection 1001c of the front end body 1001 enters the insertion hole 1031 of the end cap 1030, so that a relative angular displacement between the end cap 1030 and the front end body 1001 can be restricted.

Thereafter, the first projection 1038a and the second projection 1038b simultaneously abut against the outer peripheral edge of the front end body 1001 and the end surface 1001e thereof, respectively.

Note that the positions of the first and second projections 1038a and 1038b of the end cap 1030 are determined with respect to the front end body 1001, taking the foregoing into account. The first and second recesses 1028a and 1028b are positioned to correspond to the respective projections 1038a and 1038b.

As mentioned above, no elastic deformation (expansion) of the end cap 1030 occurs until the projections 1038a and 1038b of the end cap 1030 abut against the front end body 1001. Consequently, the end cap 1030 in which the front end body 1001 is inserted can be smoothly and easily rotated relative to the front end body 1001 substantially without a frictional resistance to thereby determine the angular position therebetween.

In this state, if an external force is exerted to further move the front end body 1001 into the end cap 1030, the outer peripheral surface of the front end body 1001 rides over the first and second projections 1038a and 1038b of the end cap 1030 simultaneously, so that the end cap 1030 can be elastically and outwardly expanded without being inclined.

When a further movement of the front end body 1001 into the end cap 1030 takes place, the first and second projections 1038a and 1038b are engaged in the corresponding first and second recesses 1028a and 1028b. Consequently, the end cap 1030 is restored due to an elastic restoring force thereof, as shown in FIG. 25. Hence, the end cap 1030 is firmly attached to the front end body 1001.

During the operation mentioned above, since the first and second projections 1038a and 1038b of the end cap 1030 simultaneously ride over the outer peripheral surface of the front end body 1001 and are then engaged in the associated recesses 1028a and 1028b, no inclination of the end cap 1030 occurs and hence, a smooth movement of the end cap can be ensured.

As can be understood from the foregoing, according to the present invention, since the relative angular position between the end cap and the front end body in the rotational direction is determined by the positioning means, prior to the elastic deformation of the end cap which is caused to engage the male and female engaging means (the first and second projections and the first and second recesses) during the relative movement of the end cap and the front end body, the determination of relative angular position between the end cap and the front end body can be smoothly carried out by a small rotational force, substantially without a frictional resistance. Consequently, no excessive force is applied to the front end body of an endoscope upon attaching the end cap thereto, and hence, the end cap can be easily attached to the front end body of the endoscope without being broken.

FIGS. 32A to 32D show inserting portions 1100A to 1100D of four different kinds of endoscopes having front end bodies 1101A to 1101D connected to the respective inserting portions.

The end caps 1130A to 1130D are respectively detachably attached to the front ends of the front end bodies 1101A to 1101D. In FIGS. 32A to 32D, the end caps are detached from the respective front end bodies as shown in FIGS. 1 to 31.

Among the four kinds of endoscopes 1100A to 1100D, the end caps 1130A, 1130B and 1130C are not compatible. The end caps 1130B and 1130D are compatible with each other, since the front bodies 1101B and 1101D are identical in the shape and size thereof.

For the endoscope 1100A, the front end body 1101A and the end cap 1130A are colored by the same color (e.g., yellow). However, for the endoscope 1100B which is not compatible or interchangeable to the endoscope 1100A, the front end body 1101B and the end cap 1130B are colored by the same color (e.g., gray) which is different from the color of the front end body 1101A and the end cap 1130A.

For the endoscope 1100C which is incompatibile to the endoscopes 1100A or 1100B, the front end body 1101B and the end cap 1130B are colored by the same color (e.g., black) which is different from the color for the endoscopes 1100A and 1100B.

For the endoscope 1100D which is compatible to the endoscope 1100B, the front end body 1101D and the end cap 1130D are colored by the same color (e.g., gray) which is the same as the color for the kind "B".

Consequently, when the end caps 1130A to 1130D are attached to the front end bodies 11001A to 1101D, any one of the end caps whose color is the same as the color of the associated front end body to which the end cap is to be attached can be selected. Namely, it is necessary for an operator to only look at the color of the end cap to correctly select the same upon attachment of the end cap to the front end body. Hence, no mounting error occurs.

It is not necessary to color the entirety of each end cap or each front end body in a specified color. Namely, it is possible to partly color the outer surfaces of the end caps and the front end bodies in the specified colors. The end caps and the front end bodies can be made of materials having the specified colors or can be painted later in the specified colors.

The number of the kinds of the endoscopes or end caps is not limited to that of the embodiment illustrated in FIG. 32. Namely, the present invention can be applied to two or more kinds of endoscopes.

Note that the end caps are made of a resilient material in the illustrated embodiment, the present invention is not limited thereto. Namely, the end caps can be made of plastics or metal, etc. In this alternative, the end caps can be secured to the front end body by a screw or a click mechanism, etc.

As can be understood from the foregoing, according to the present invention, since the end cap which is detachably attached to the front end body of an endoscope can be certainly and visually identified, there is no danger that an incompatible end cap could be attached to the wrong front end body by mistake, and hence, no breakage of the front end body due to a strong force which would be otherwise applied thereto takes place.

Since the color of the end cap is different from the color of the plastic portion of the front end body, the boundary portion between the rear end of the end cap and the exposed outer peripheral surface of the front end body can be clearly viewed, when the end cap is detached from the front end body. Consequently, an appropriate force can be applied to a correct position, i.e., the boundary portion, so that the end cap can be easily and certainly detached from the front end body without breaking the front end body, etc.

Note that the present invention is not limited to the illustrated embodiments. For instance, the color of the end cap and the exposed surface of the front end body can be colored by any colors which can be clearly distinguished. The difference in color is present at least at the boundary portion between the end cap and the exposed surface of the front end body, and the remaining portions of the end cap and the front end body can be of any colors. There is no limitation to the coloring method. It is possible to paint the end cap and the exposed surface of the front end body in desired colors or to make them of materials colored by desired colors.

As can be seen from the above discussion, according to the present invention, since the boundary portion between the rear end of the end cap and the exposed surface portion of the front end body can be easily, clearly and visually confirmed, an appropriate force can be applied to a correct position, i.e., the boundary portion to detach the end cap from the front end body without a fear of a breakage of the front end body, etc.

We claim:

1. An endoscope including a front end body which has a circular cross section and which is provided at a front end of an inserting portion of said endoscope, and a substantially cylindrical end cap of a resilient material, which is detachably attached to said front end body, said endoscope further comprising:
 - a partial projection which is provided on said front end of said front end body to project forward, at least one peripheral groove provided on an outer peripheral surface of said partial projection and at least one peripheral groove provided on an outer peripheral surface of said front end body;
 - an insertion hole formed in said end cap so that said projection is fitted in said insertion hole;
 - a plurality of projections provided on said end cap including a first projection to be fitted in said peripheral groove provided on said front end body and a second projection disposed axially from said first projection to be fitted in said peripheral groove provided in said partial projection;
 - wherein when said end cap is attached to said front end body from said front end of said latter, said partial projection of said front end body is fitted in said insertion hole of said end cap to determine a relative angular position therebetween in a rotational direction, and thereafter, said projections of said end cap are fitted simultaneously in said groove of said front end body and said groove of said partial projection.

2. A front end structure of an endoscope in accordance with claim 1 wherein said at least one peripheral groove provided on said partial projection and said at least one peripheral groove provided on said outer peripheral surface of said front end body are circumferentially offset from one another and together extend substantially entirely about the front end body.

3. A front end structure of an endoscope in accordance with claim 2 wherein said end cap first projection substantially fills said at least one peripheral groove provided on said outer peripheral surface of said front end body and said end cap second projection substantially fills said at least one peripheral groove provided on said outer peripheral surface of said front end body partial projection.

* * * * *

UNITED STATES PATENT AND TRADEMARK OFFICE
CERTIFICATE OF CORRECTION

PATENT NO. : 5,746,695
DATED : May 5, 1998
INVENTOR(S) : Naoki Yasui, et al.

It is certified that error appears in the above-identified patent and that said Letters Patent is hereby corrected as shown below:

On the title page, Item [30], correct the Foreign Application Priority Data to read as follows:

[30]   Foreign Application Priority Data

Jan. 24, 1994   [JP]   ....................6-005491

Signed and Sealed this

Fourth Day of August, 1998

Attest:

BRUCE LEHMAN

Attesting Officer

Commissioner of Patents and Trademarks